(12) United States Patent
Saito

(10) Patent No.: US 11,369,294 B2
(45) Date of Patent: Jun. 28, 2022

(54) ENDOSCOPE SYSTEM, PROCESSOR DEVICE, AND METHOD OF OPERATING ENDOSCOPE SYSTEM

(71) Applicant: FUJIFILM Corporation, Tokyo (JP)

(72) Inventor: Takaaki Saito, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 174 days.

(21) Appl. No.: 16/864,682

(22) Filed: May 1, 2020

(65) Prior Publication Data

US 2020/0352488 A1 Nov. 12, 2020

(30) Foreign Application Priority Data

May 9, 2019 (JP) .............................. JP2019-089018

(51) Int. Cl.
| | |
|---|---|
| A61B 5/1455 | (2006.01) |
| A61B 5/1459 | (2006.01) |
| A61B 5/00 | (2006.01) |
| A61B 1/06 | (2006.01) |
| A61B 1/00 | (2006.01) |
| A61B 1/018 | (2006.01) |

(52) U.S. Cl.
CPC ...... *A61B 5/14552* (2013.01); *A61B 1/00009* (2013.01); *A61B 1/00087* (2013.01); *A61B 1/018* (2013.01); *A61B 1/0638* (2013.01); *A61B 5/1459* (2013.01); *A61B 5/742* (2013.01)

(58) Field of Classification Search
None
See application file for complete search history.

(56) References Cited

U.S. PATENT DOCUMENTS

2013/0030268 A1* 1/2013 Saito .................... A61B 1/0653
600/325

FOREIGN PATENT DOCUMENTS

JP 2014-076375 A 5/2014

\* cited by examiner

*Primary Examiner* — Marjan Fardanesh
(74) *Attorney, Agent, or Firm* — Studebaker & Brackett PC

(57) ABSTRACT

A measurement value calculation section calculates the actual measurement value of the hemoglobin concentration of an object to be observed and the actual measurement value of an oxygen saturation thereof on the basis of a plurality of first spectral images. A relative value calculation section calculates the relative value of the hemoglobin concentration and the relative value of the oxygen saturation on the basis of the actual measurement value and the reference value of the hemoglobin concentration and the actual measurement value and the reference value of the oxygen saturation. An image generation section generates a relative value image obtained from the imaging of the relative value of the hemoglobin concentration and/or the relative value of the oxygen saturation, and displays the relative value image on a display unit.

13 Claims, 18 Drawing Sheets

| ILLUMINATION LIGHT | IMAGE PICKUP (IMAGE SIGNAL) |
|---|---|
| FIRST BLUE LIGHT BS GREEN LIGHT G RED LIGHT R | (Bc, Gc, Rc) |

FIG. 7

| SUBJECT | | ILLUMINATION LIGHT | | IMAGE PICKUP (IMAGE SIGNAL) | | |
|---|---|---|---|---|---|---|
| ISCHEMIA EVALUATION MODE | FIRST OBJECT TO BE OBSERVED | FIRST LIGHT EMISSION | FIRST BLUE LIGHT BS GREEN LIGHT G RED LIGHT R | FIRST IMAGE PICKUP | (B1m, G1m, R1m) | FIRST SPECTRAL IMAGE |
| | | SECOND LIGHT EMISSION | SECOND BLUE LIGHT BL GREEN LIGHT G RED LIGHT R | SECOND IMAGE PICKUP | (B2m, G2m, R2m) | |

FIG. 8

| REFERENCE VALUE CALCULATION MODE | SUBJECT | ILLUMINATION LIGHT | | IMAGE PICKUP (IMAGE SIGNAL) | |
|---|---|---|---|---|---|
| | | | | FIRST IMAGE PICKUP | |
| | SECOND OBJECT TO BE OBSERVED | FIRST LIGHT EMISSION | FIRST BLUE LIGHT BS GREEN LIGHT G RED LIGHT R | (B1n, G1n, R1n) | |
| | | SECOND LIGHT EMISSION | SECOND BLUE LIGHT BL GREEN LIGHT G RED LIGHT R | SECOND IMAGE PICKUP (B2n, G2n, R2n) | SECOND SPECTRAL IMAGE |

ENDOSCOPE SYSTEM, PROCESSOR DEVICE, AND METHOD OF OPERATING ENDOSCOPE SYSTEM

CROSS-REFERENCE TO RELATED APPLICATIONS

This application claims priority under 35 U.S.C § 119(a) to Japanese Patent Application No. 2019-089018 filed on 9 May 2019. The above application is hereby expressly incorporated by reference, in its entirety, into the present application.

BACKGROUND OF THE INVENTION

1. Field of the Invention

The present invention relates to an endoscope system, a processor device, and a method of operating an endoscope system that are used during surgery for resecting a tumor portion, such as a cancer, or used for processing to be performed after the surgery.

2. Description of the Related Art

In recent years, laparoscopic surgery, which performs surgery using a laparoscope, has attracted attention. For example, in the case of the resection of a colorectal cancer using a laparoscope, an operator inserts a laparoscope and a treatment tool for surgery into the abdominal cavity through a trocar penetrating the patient's abdomen. Then, the operator inflates the inside of the abdominal cavity with insufflation gas formed of carbon dioxide, and displays the image of the inside of the abdominal cavity on a monitor. After that, the operator resects a portion of the large intestine where a primary tumor has been formed while observing the image of the inside of the abdominal cavity displayed on the monitor. The large intestine that is cut off by the resection of the primary tumor is sutured by an automatic suturing device or the like.

After the surgery, in the process of the normal agglutination of a wound to be performed after suture, the activation of fibroblasts of the tissues usually occurs after two or three days from the completion of the suture and the agglutination is completed after about seven days. However, in a case where agglutination is inhibited by some factors during the agglutination between the tissues, sufficient agglutination does not occur between the tissues. For this reason, the failure of the sutures where a part of or all of a sutured portion is broken may occur.

It is important to connect the intestinal canal to a portion having a blood flow as much as possible to prevent the postoperative failure of the sutures in surgery, such as intestinal anastomosis to be performed after the resection of a colorectal cancer. Basically, the degree of a blood flow is visually determined on the basis of the color tone of the intestinal canal. However, angiography using the administration of a fluorescent agent, such as indocyanine green (ICG), is also widely used to visualize the boundary of ischemia that is difficult to be visually recognized. In a method using the administration of ICG, it is necessary to wait several minutes after intravenous injection and a dedicated light source and a camera are required for the observation of a fluorescence image. Further, since the medical agent remains in the blood after the medical agent is administered once, there is also a problem that it is difficult to administer the medical agent again and to observe a fluorescence image again. For this reason, the utilization of the visualization or imaging of the oxygen saturation of hemoglobin, which is included in an object to be observed, using an endoscope, that is, the utilization of oxygen saturation imaging is expected.

JP2014-076375A discloses an endoscope system comprising setting change means for changing reference information, which prescribes a correlation between an oxygen saturation and a pixel value obtained from the image pickup of a portion to be observed, according to the properties of the portion to be observed in oxygen saturation imaging using an endoscope. Accordingly, highly reliable information about an oxygen saturation can be acquired.

SUMMARY OF THE INVENTION

In a case where the oxygen saturation imaging of an endoscope is utilized, information about the level of an oxygen saturation can be obtained from imaged information about an oxygen saturation. However, a congestive region where blood is accumulated in a blood vessel and an ischemic region where the amount of blood in a blood vessel is small are present in a region where an oxygen saturation is low. Accordingly, since there is a case where it is difficult to determine a boundary between, for example, a congestive portion, an ischemic portion, or a normal portion and an ischemic portion or the like by only information about an oxygen saturation, only the information about an oxygen saturation is not necessarily sufficient as information for determination for the prevention of the failure of the sutures after surgery.

An object of the invention is to provide an endoscope system, a processor device, and a method of operating an endoscope system that can easily and stably display a determination index for ischemia or congestion which can be used as information for the determination of a resection position or an anastomosis position where the failure of the sutures hardly occurs.

In order to solve the problem in the related art, an endoscope system according to an aspect of the invention comprises: a measurement value calculation section that calculates a first actual measurement value of a concentration of hemoglobin included in an object to be observed and a first actual measurement value of an oxygen saturation of hemoglobin included in the object to be observed on the basis of a plurality of first spectral images; a relative value calculation section that calculates a relative value of the concentration and a relative value of the oxygen saturation on the basis of the first actual measurement value of the concentration, a reference value of the concentration of hemoglobin included in the object to be observed, the first actual measurement value of the oxygen saturation, and a reference value of the oxygen saturation of hemoglobin included in the object to be observed; an image generation section that generates a relative value image obtained from imaging of at least one of the relative value of the concentration or the relative value of the oxygen saturation; and a display unit that displays the relative value image.

It is preferable that the measurement value calculation section comprises a reference value calculation section calculating the reference value of the concentration and the reference value of the oxygen saturation on the basis of a plurality of second spectral images.

It is preferable that the endoscope system further comprises a reference value-calculation-instruction receiving section receiving an instruction to calculate the reference value of the concentration and the reference value of the oxygen saturation, and the reference value calculation section calculates the reference value of the concentration and the reference value of the oxygen saturation on the basis of the instruction.

It is preferable that the reference value calculation section calculates the reference value of the concentration or the reference value of the oxygen saturation by averaging second actual measurement values of the concentration calculated for pixels of the plurality of second spectral images or second actual measurement values of the oxygen saturation calculated for pixels of the plurality of second spectral images.

It is preferable that the measurement value calculation section comprises a signal ratio calculation section obtaining a signal ratio dependent on the concentration on the basis of the plurality of first spectral images or the plurality of second spectral images, a correlation storage section storing a correlation between the concentration and the signal ratio, and an actual measurement value calculation section calculating the first actual measurement value or the second actual measurement value of the concentration corresponding to the signal ratio on the basis of the correlation.

It is preferable that the first spectral images are images obtained from image pickup of a first object to be observed including a lesion and the second spectral images are images obtained from image pickup of a second object to be observed not including a lesion.

It is preferable that the relative value image includes a hemoglobin concentration image obtained from imaging of the relative value of the concentration, an oxygen saturation image obtained from imaging of the relative value of the oxygen saturation, and a determination index image obtained from imaging of the relative value of the concentration and the relative value of the oxygen saturation.

It is preferable that the image generation section generates the hemoglobin concentration image by converting the relative value of the concentration into a pseudo-color image using a color table for the concentration storing pseudo-color information changing according to the concentration, and generates the oxygen saturation image by converting the relative value of the oxygen saturation into a pseudo-color image using a color table for the oxygen saturation storing pseudo-color information changing according to the oxygen saturation.

It is preferable that the image generation section generates the determination index image by assigning the relative value of the concentration to a luminance channel and assigning the relative value of the oxygen saturation to two color difference channels.

It is preferable that the endoscope system further comprises a display image selection section receiving a selection of a display image and the display unit displays at least one of the hemoglobin concentration image, the oxygen saturation image, or the determination index image according to the selection received by the display image selection section.

It is preferable that the display unit displays both the hemoglobin concentration image and the oxygen saturation image on the same screen.

A processor device according to another aspect of the invention comprises: an image acquisition unit that receives a plurality of first spectral images from an endoscope device acquiring the plurality of first spectral images; a measurement value calculation section that calculates a first actual measurement value of a concentration of hemoglobin included in an object to be observed and a first actual measurement value of an oxygen saturation of hemoglobin included in the object to be observed on the basis of the plurality of first spectral images; a relative value calculation section that calculates a relative value of the concentration and a relative value of the oxygen saturation on the basis of the first actual measurement value of the concentration, a reference value of the concentration of hemoglobin included in the object to be observed, the first actual measurement value of the oxygen saturation, and a reference value of the oxygen saturation of hemoglobin included in the object to be observed; and an image generation section that generates a relative value image obtained from imaging of at least one of the relative value of the concentration or the relative value of the oxygen saturation.

A method of operating an endoscope system according to still another aspect of the invention comprises: an actual measurement value calculation step of causing a measurement value calculation section to calculate a first actual measurement value of a concentration of hemoglobin included in an object to be observed and a first actual measurement value of an oxygen saturation of hemoglobin included in the object to be observed on the basis of a plurality of first spectral images; a relative value calculation step of causing a relative value calculation section to calculate a relative value of the concentration and a relative value of the oxygen saturation on the basis of the first actual measurement value of the concentration, a reference value of the concentration of hemoglobin included in the object to be observed, the first actual measurement value of the oxygen saturation, and a reference value of the oxygen saturation of hemoglobin included in the object to be observed; an image generation step of causing an image generation section to generate a relative value image obtained from the imaging of the relative value of the concentration and/or the relative value of the oxygen saturation; and a display step of causing a display unit to display the relative value image.

According to the invention, it is possible to easily and stably provide a determination index for ischemia or congestion that can be used as information for the determination of a resection position or an anastomosis position where the failure of the sutures hardly occurs.

BRIEF DESCRIPTION OF THE DRAWINGS

FIG. 7 is a diagram illustrating a light emission pattern and the like in an ischemia evaluation mode.

FIG. 8 is a diagram illustrating a light emission pattern and the like in a reference value calculation mode.

DESCRIPTION OF THE PREFERRED EMBODIMENTS

Figure 1:
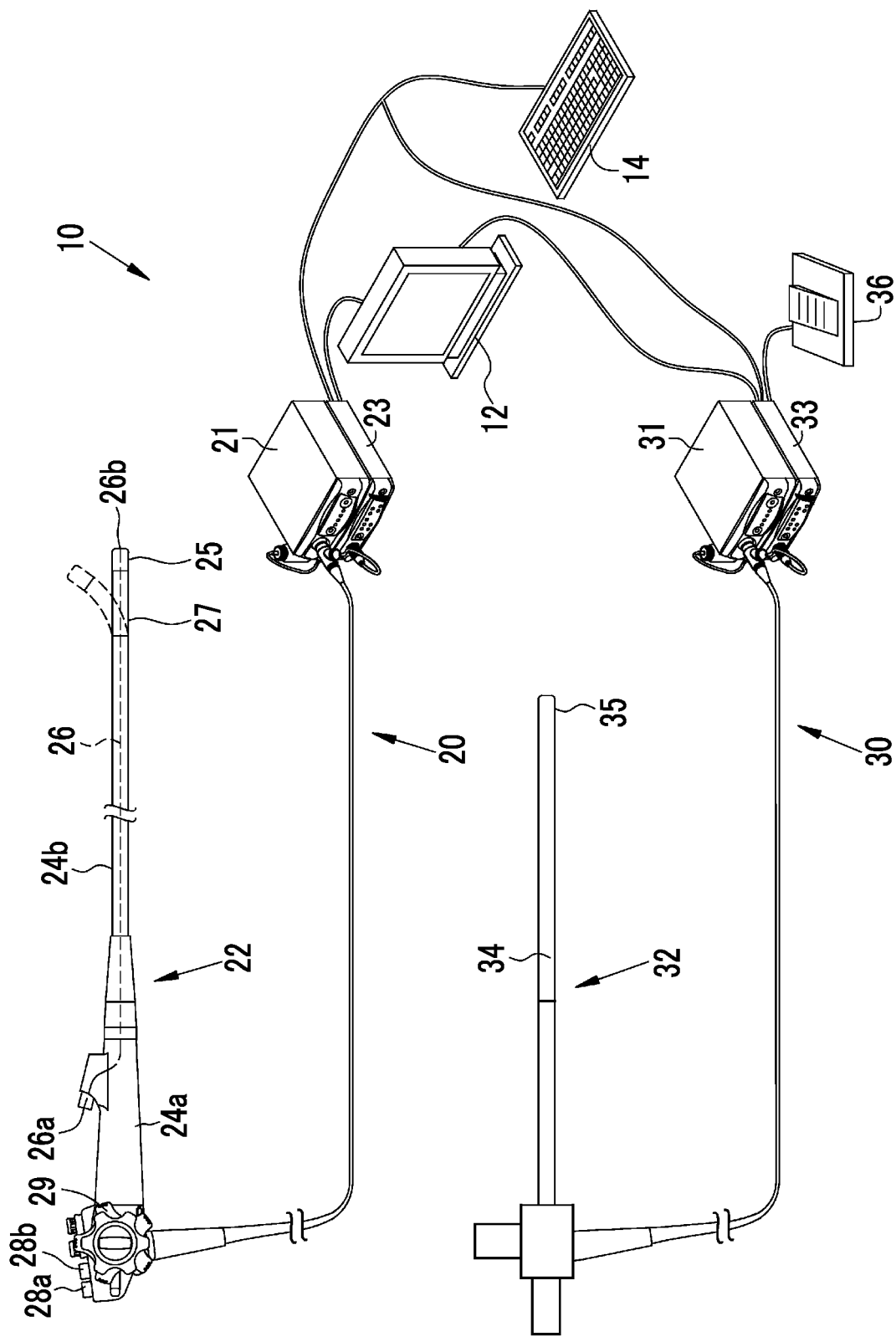
FIG. 1 is a diagram showing the appearance of a medical device system.

As shown in FIG. 1, in this embodiment, an endoscope system 10 includes an endoscope system 20 for lumen and an endoscope system 30 for abdominal cavity and is used for the resection of a tumor portion formed in the large intestine. First, before the resection of a tumor portion, the endoscope system 20 for lumen is used to detect the tumor portion formed in the large intestine and to mark a certain range (resection range) including the tumor portion. Then, the endoscope system 30 for abdominal cavity is used to resect the marked resection range of the large intestine and to suture the large intestine that is cut off by the resection of the tumor portion. Finally, the endoscope system 20 for lumen is used to confirm whether or not a sutured portion is structurally agglutinated.

The endoscope system 20 for lumen comprises a light source device 21 for lumen that generates light illuminating the inside of the lumen, an endoscope device 22 for lumen that irradiates the inside of the lumen with the light generated from the light source device 21 for lumen and picks up the reflected image of the inside of the lumen, and a processor device 23 for lumen that performs image processing on image signals obtained from image pickup performed by the endoscope device 22 for lumen. The processor device 23 for lumen is connected to a display device 12 (display unit) and an input device 14. The display device 12 displays an endoscopic image that is obtained from the image processing, and the like; and the input device 14 is formed of a keyboard or the like. The display device 12 is, for example, a monitor.

The endoscope device 22 for lumen picks up the image of an object to be observed and obtains the image. The endoscope device 22 for lumen is a flexible endoscope; and comprises an endoscope operation unit 24a for lumen, a flexible endoscope-insertion part 24b for lumen, and a scope-distal end part 25 that is provided at the distal end of the insertion part, irradiates the inside of the lumen with light, and picks up the reflected image of the inside of the lumen. The endoscope device 22 for lumen includes a bendable part 27 that is provided on the distal end side of the endoscope-insertion part 24b for lumen. The endoscope operation unit 24a for lumen includes angle knobs 29 that are used for an operation for bending the bendable part 27. The bendable part 27 is operated to be bent on the basis of the operation of the angle knobs 29, so that the scope-distal end part 25 is caused to face in a desired direction. The scope-distal end part 25 is provided with a jet port (not shown) that jets cleaning liquid toward an object to be observed.

Further, the endoscope operation unit 24a for lumen is provided with a mode switching part 28a that is used for an operation for switching an observation mode and a reference value-calculation-instruction part 28b that receives an instruction to calculate a reference value, in addition to the angle knobs 29.

Furthermore, the endoscope device 22 for lumen is provided with a forceps channel 26 into which a treatment tool, such as hemostatic probes, is to be inserted. A treatment tool is inserted into the forceps channel 26 from a forceps inlet 26a provided at the operation unit, and the treatment tool inserted into the forceps channel 26 protrudes from a forceps outlet 26b provided at the distal end part.

The endoscope system 20 for lumen has at least three modes, that is, a normal mode, an ischemia evaluation mode, and a reference value calculation mode. In the normal mode, an image having a natural hue (hereinafter, referred to as a normal image), which is obtained from the image pickup of a part to be observed using white light as illumination light, is displayed on the display device 12. In the ischemia evaluation mode, the relative value of the concentration of hemoglobin included in an object to be observed (cHb, hereinafter, referred to as a hemoglobin concentration) and the relative value of the oxygen saturation of hemoglobin included in the object to be observed ($StO_2$, hereinafter, referred to as an oxygen saturation) are calculated, and the relative value of a hemoglobin concentration and the relative value of an oxygen saturation or a relative value image, which is obtained from the imaging of the relative value of a hemoglobin concentration and the relative value of an oxygen saturation, is displayed on the display device 12. The relative value image is a determination index for ischemia or congestion that can be used as information for the determination of a resection position or an anastomosis position where the failure of the sutures hardly occurs. An operator and the like can evaluate the state of ischemia of the object to be observed using the relative value image as a determination index.

In the reference value calculation mode, the hemoglobin concentration and the oxygen saturation of a reference object to be observed are calculated and the reference value of a hemoglobin concentration and the reference value of an oxygen saturation, which have been already set, are updated on the basis of the calculated hemoglobin concentration and the calculated oxygen saturation. The two modes, that is, the normal mode and the ischemia evaluation mode can be switched according to an instruction given from the mode switching part 28a or the like of the endoscope device 22 for lumen.

In the ischemia evaluation mode, usually, the relative value of a hemoglobin concentration and the relative value of an oxygen saturation are calculated from the first actual measurement value of a hemoglobin concentration, the first actual measurement value of an oxygen saturation, the reference value of a hemoglobin concentration, and the reference value of an oxygen saturation. The first actual measurement value of a hemoglobin concentration and the first actual measurement value of an oxygen saturation are based on a plurality of spectral images (first spectral images) that are obtained from image pickup using a region, of which the state of ischemia is desired to be evaluated, as an object to be observed; and the reference value of a hemoglobin concentration and the reference value of an oxygen saturation are based on a plurality of spectral images (second spectral images) that are obtained from image pickup using a region, of which the state of ischemia is desired to be set as a reference, as an object to be observed. A hemoglobin concentration and/or an oxygen saturation can be relatively evaluated in the ischemia evaluation mode. Accordingly, the ischemia evaluation mode does not mean a mode where only ischemia is evaluated, and the state of ischemia, congestion, hyperemia, or the like can also be evaluated in the ischemia evaluation mode in addition to an oxygen saturation.

The state of ischemia is a state that is evaluated from both the value of an oxygen saturation and the value of the amount of blood, and is a state where an oxygen saturation is relatively low and the amount of blood is relatively small. Likewise, the state of congestion is also a state that is evaluated from both the value of an oxygen saturation and the value of the amount of blood, and is a state where an oxygen saturation is relatively low and the amount of blood is relatively large.

Since an object of which the state of ischemia is desired to be evaluated is usually an object (a first object to be observed) including a lesion, the first spectral images are the images of the first object to be observed including a lesion. On the other hand, the reference value of a hemoglobin concentration and the reference value of an oxygen saturation are obtained using a plurality of spectral images (second spectral images) that are obtained from image pickup using an object, which is different from the object of which the state of ischemia is desired to be evaluated, as an object to be observed. Accordingly, since an object, which is desired to be set to a reference value, is usually an object (a second object to be observed) not including a lesion, the second spectral images are the images of the second object to be observed not including a lesion.

The reference value calculation mode is a mode that is automatically switched in a case where an instruction to calculate a reference value is given by the reference value-calculation-instruction part 28b or the like of the endoscope device 22 for lumen. For example, an operator gives an instruction to calculate a reference value by the reference value-calculation-instruction part 28b or the like while directing the scope of the endoscope device 22 for lumen to a region, which is desired to be set to a reference value, as an object to be observed. A mode is switched to the reference value calculation mode according to this instruction. After the reference value is updated, the mode automatically returns to a mode that has been set before the mode is switched to the reference value calculation mode.

The endoscope system 30 for abdominal cavity comprises a light source device 31 for abdominal cavity that generates light illuminating the inside of the abdominal cavity, an endoscope device 32 for abdominal cavity that irradiates the inside of the abdominal cavity with the light generated from the light source device 31 for abdominal cavity and picks up the reflected image of the inside of the abdominal cavity, and a processor device 33 for abdominal cavity that performs image processing on image signals obtained from image pickup performed by the endoscope device 32 for abdominal cavity. The processor device 33 for abdominal cavity is connected to the display device 12 and the input device 14. The endoscope device 32 for abdominal cavity picks up the image of an object to be observed and obtains the image. The endoscope device 32 for abdominal cavity is a rigid endoscope; and comprises a rigid endoscope-insertion part 34 for abdominal cavity, and an endoscope-distal end part 35 for abdominal cavity that is provided at the distal end of the endoscope-insertion part for abdominal cavity, irradiates the inside of the abdominal cavity with light, and picks up the reflected image of the inside of the abdominal cavity.

Further, the endoscope system 30 for abdominal cavity has at least three modes, that is, a normal mode, an ischemia evaluation mode, and a reference value calculation mode that are the same as those of the endoscope system 20 for lumen. Two modes, that is, the normal mode and the ischemia evaluation mode can be switched according to an instruction of a foot switch 36 or the like connected to the processor device 33 for abdominal cavity. The reference value calculation mode is a mode that is automatically switched in a case where an instruction to calculate a reference value is given by the input device 14 or the like of the endoscope system 30 for abdominal cavity. These three modes are the same as described for the endoscope system 20 for lumen.

Figure 2:
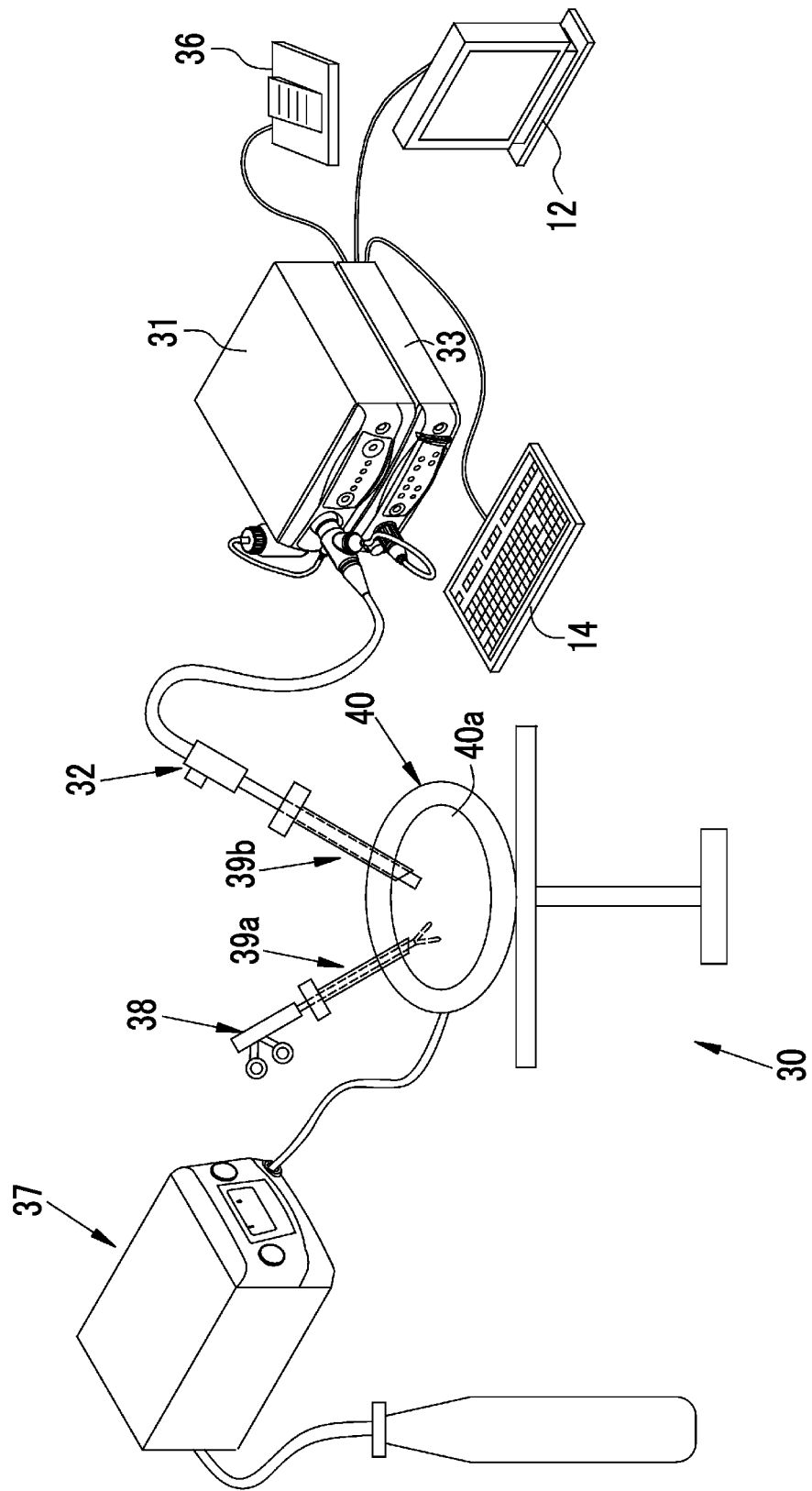
FIG. 2 is a diagram showing the appearance of an endoscope system for abdominal cavity.

As shown in FIG. 2, to observe the inside of the abdominal cavity and to perform surgery to remove a tumor portion, an insufflation device 37, a treatment tool 38, and trocars 39a and 39b are used in the endoscope system 30 for abdominal cavity in addition to the light source device 31 for abdominal cavity, the endoscope device 32 for abdominal cavity, and the processor device 33 for abdominal cavity. In the endoscope system 30 for abdominal cavity, first, carbon dioxide ($CO_2$) gas is supplied to the inside 40a of the abdominal cavity of a patient 40 from the insufflation device 37 to insufflate the abdominal cavity of the patient 40. Accordingly, a field of view or a surgical field in the abdominal cavity can be ensured.

Then, the treatment tool 38 is inserted into the inside 40a of the abdominal cavity of the patient 40 through the trocar 39a, and the endoscope device 32 for abdominal cavity is inserted into the inside 40a of the abdominal cavity of the patient 40 through the trocar 39b. Each of these trocars 39a and 39b comprises a hollow pipe made of metal and an operator grip part, and an operator causes the sharp distal end of the hollow pipe to penetrate the abdomen of the patient 40 in a state where the operator grips the operator grip part, so that the hollow pipe is inserted into the body cavity. The treatment tool 38 and the endoscope device 32 for abdominal cavity are inserted into the trocars 39a and 39b of which the hollow pipes are inserted into the abdominal cavity in this way.

The endoscope system 20 for lumen will be described below as a representative. Since the endoscope system 30 for abdominal cavity is the same as the endoscope system 20 for lumen, the description of the same portions will be omitted.

Figure 3:
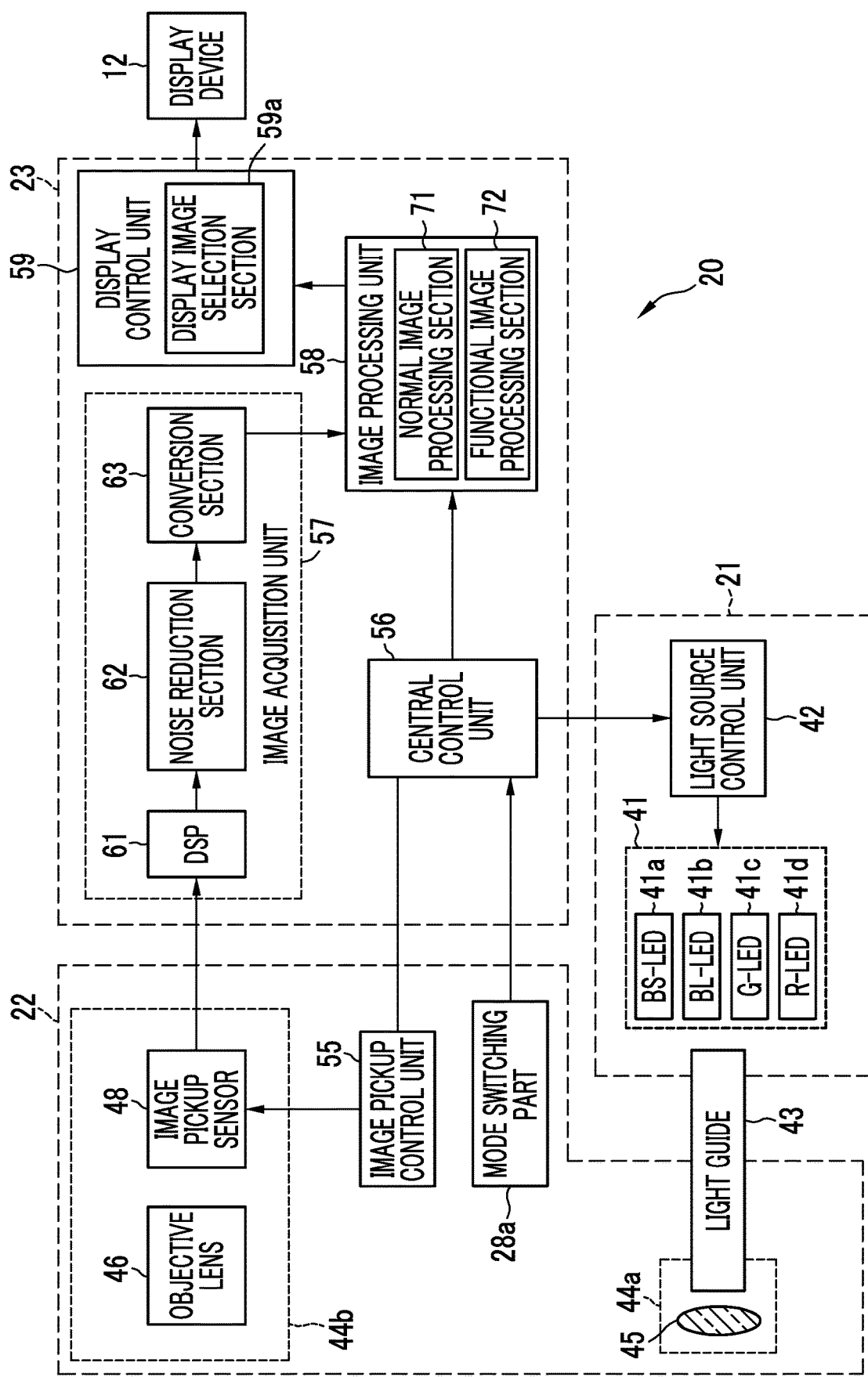
FIG. 3 is a block diagram of an endoscope system for lumen.

As shown in FIG. 3, the light source device 21 for lumen comprises a light source 41 and a light source control unit 42. The light source 41 includes, for example, a plurality of semiconductor light sources, and these semiconductor light sources are turned on or off, respectively. In a case where the light source 41 is turned on, illumination light illuminating an object to be observed is emitted. In this embodiment, the light source 41 includes four color LEDs, that is, a blue short-wavelength light emitting diode (BS-LED) 41a, a blue long-wavelength light emitting diode (BL-LED) 41b, a green light emitting diode (G-LED) 41c, and a red light emitting diode (R-LED) 41d.

The BS-LED 41a emits a first blue light BS having a wavelength range of 450±10 nm. The BL-LED 41b emits a second blue light BL which has a wavelength range of 470±10 nm and of which the wavelength is longer than the wavelength of the first blue light BS. The G-LED 41c emits a green light G having a wavelength range of 500 nm to 600 nm. The R-LED 41d emits a red light R having a wavelength range of 620±20 nm. The central wavelength and the peak wavelength of each color light may be equal to each other or may be different from each other.

The light source control unit 42 independently inputs control signals to the respective LEDs 41a to 41d to independently control the turn-on and turn-off of the respective LEDs 41a to 41d, the amounts of the lights that are emitted from the respective LEDs 41a to 41d in a case where the respective LEDs 41a to 41d are turned on, and the like. The control of the turn-on and turn-off performed by the light source control unit 42 varies in each observation mode. In the normal mode, the light source control unit 42 simultaneously turns on the BS-LED 41a, the G-LED 41c, and the R-LED 41d to simultaneously emit the first blue light BS, the green light G, and the red light R.

In the ischemia evaluation mode, the light source control unit 42 alternately performs first light emission where the BS-LED 41a, the G-LED 41c, and the R-LED 41d are simultaneously turned on to simultaneously emit the first blue light BS, the green light G, and the red light R and second light emission where the BL-LED 41b, the G-LED 41c, and the R-LED 41d are simultaneously turned on to simultaneously emit the second blue light BS, the green light G, and the red light R.

The respective lights emitted from the respective LEDs 41a to 41d are incident on a light guide 43. The light guide 43 is built in the endoscope device 22 for lumen and a universal cord. The universal cord is a cord that connects the endoscope device 22 for lumen to the light source device 21 and the processor device 23. The light guide 43 transmits light up to the scope-distal end part 25 of the endoscope device 22 for lumen.

The endoscope device 22 for lumen is formed of an electronic endoscope; and comprises an illumination optical system 44a that irradiates an object to be observed with the light guided by the light guide 43, an image pickup optical system 44b that picks up the image of the object to be observed, and an image pickup control unit 55. Further, the endoscope device 22 for lumen comprises connector parts (not shown) that allow the endoscope device 22 for lumen to be attachably and detachably connected to the light source device 21 for lumen and the processor device 23 for lumen.

The scope-distal end part 25 of the endoscope device 22 for lumen is provided with the illumination optical system 44a and the image pickup optical system 44b. The illumination optical system 44a includes an illumination lens 45. An object to be observed is irradiated with the illumination light emitted from the light guide 43 through the illumination lens 45. The image pickup optical system 44b includes an objective lens 46 and an image pickup sensor 48. The objective lens 46 causes light, which returns from the object to be observed illuminated with the illumination light, to be incident on the image pickup sensor 48. Accordingly, the image of the object to be observed is formed on the image pickup sensor 48.

Figure 4:
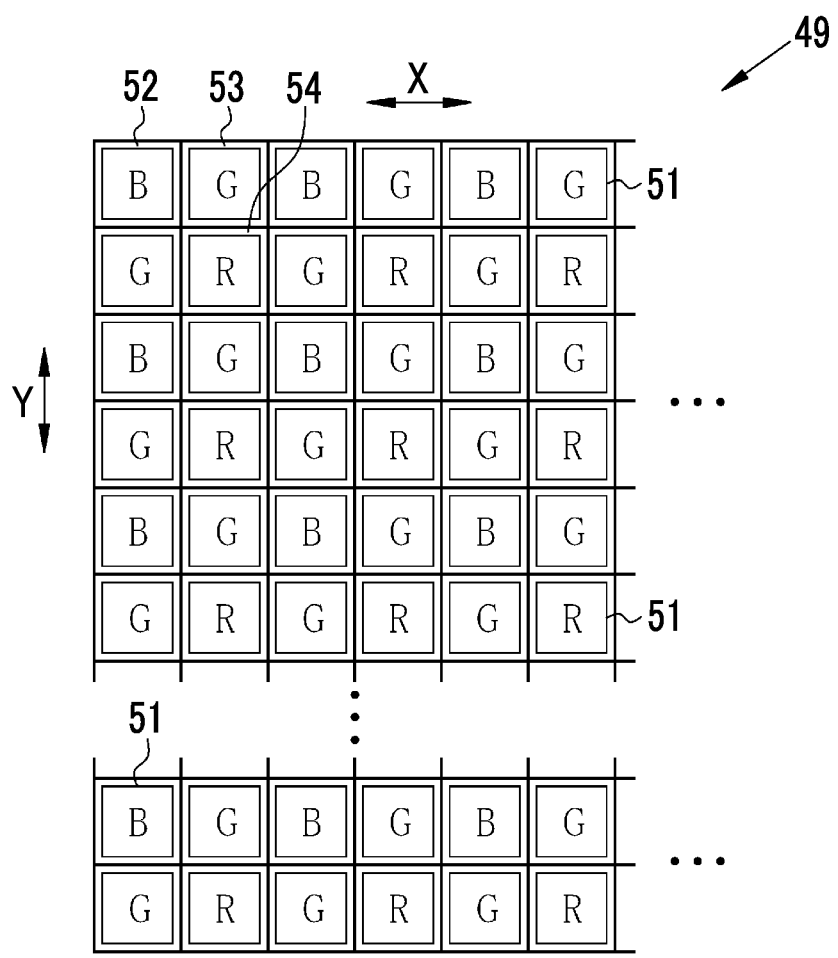
FIG. 4 is a diagram illustrating the pixels of an image pickup sensor.

The image pickup sensor 48 is a color image pickup sensor that picks up the image of an object to be observed illuminated with illumination light and outputs image signals. As shown in FIG. 4, a plurality of pixels 51 are two-dimensionally arrayed on an image pickup surface 49 of the image pickup sensor 48 in the form of a matrix in a row direction (X direction) and a column direction (Y direction). One pixel 51 is provided with any one of a blue (B) color filter 52, a green (G) color filter 53, and a red (R) color filter 54. The array of the respective color filters 52 to 54 is Bayer array, and the G-color filters 53 are arranged on every other pixel in a checker pattern and the B-color filters 52 and the R-color filters 54 are arranged on the other pixels in a square lattice pattern.

Figures 5, 6:
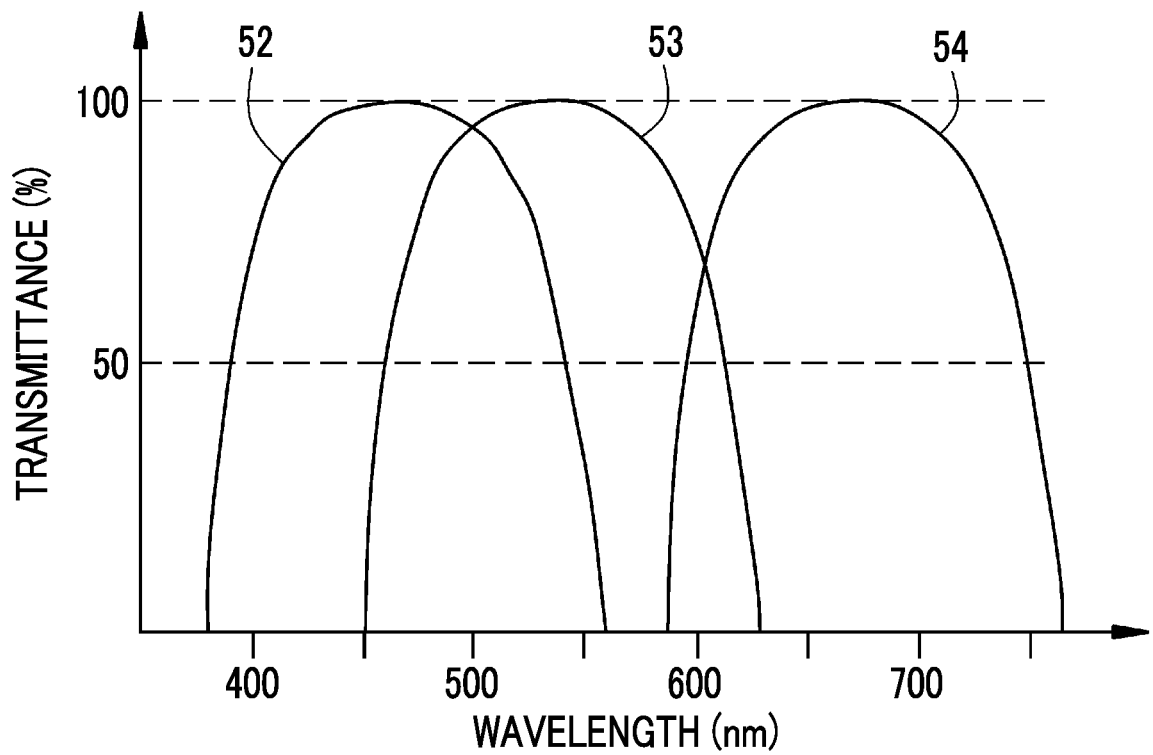
FIG. 5 is a diagram illustrating color filters.
FIG. 6 is a diagram illustrating a light emission pattern in a normal mode.

As shown in FIG. 5, the B-color filter 52 transmits light having a wavelength range of 380 nm to 560 nm. The G-color filter 53 transmits light having a wavelength range of 450 nm to 630 nm. The R-color filter 54 transmits light having a wavelength range of 580 nm to 760 nm. For this reason, a B pixel has sensitivity in a wavelength range of 450±10 nm of the first blue light BS and a wavelength range of 470±10 nm of the second blue light BL. A G pixel has sensitivity in a wavelength range of 500 nm to 600 nm of the green light G. An R pixel has sensitivity in a wavelength range of 640±20 nm of the red light R.

A charge coupled device (CCD) image pickup sensor or a complementary metal-oxide semiconductor (CMOS) image pickup sensor can be used as the image pickup sensor 48 (as FIG. 3).

A complementary color image pickup sensor comprising complementary color filters corresponding to cyan (C), magenta (M), yellow (Y), and green (G) may be used instead of the primary color image pickup sensor 48. In a case where a complementary color image pickup sensor is used, image signals corresponding to four colors of C, M, Y, and G are output. Accordingly, in a case where image signals corresponding to four colors of C, M, Y, and G are converted into image signals corresponding to three colors of R, G, and B by complementary color-primary color conversion, image signals corresponding to the same respective colors of R, G, and B as those of the image pickup sensor 48 can be obtained.

The image pickup sensor 48 receives light, which is incident from the objective lens 46, by a light-receiving surface (image pickup surface) thereof, photoelectrically converts the received light, and outputs image pickup signals (analog signals). The image pickup control of the image pickup sensor 48 is performed by the image pickup control unit 55.

The image pickup control unit 55 is electrically connected to the light source control unit 42, and performs image pickup control according to the light emission control of the light source control unit 42. As shown in FIG. 6, in the normal mode, the image pickup control unit 55 controls the image pickup sensor 48 to cause the image pickup sensor 48 to pick up the image of an object to be observed, which is being illuminated with the first blue light BS, the green light G, and the red light R emitted on the basis of the control of the light source control unit 42, for each frame. Accordingly, Bc image signals are output from the B pixels of the image pickup sensor 48, Gc image signals are output from the G pixels, and Rc image signals are output from the R pixels. The image pickup control unit 55 synchronizes the exposure time of the image pickup sensor 48 with the illumination time of illumination light.

In the ischemia evaluation mode, the image pickup control unit 55 makes image pickup control in the first light emission be different from the image pickup control in the second light emission. Specifically, in the first light emission, as shown in FIG. 7, the image pickup control unit 55 performs first image pickup where the image of the first object to be observed, which is being illuminated with the first blue light BS, the green light G, and the red light R simultaneously emitted during the first light emission, is picked up for each frame. Accordingly, during the first image pickup, B1m image signals are output from the B pixels of the image pickup sensor 48, G1m image signals are output from the G pixels, and R1m image signals are output from the R pixels. Further, the image pickup control unit 55 performs second image pickup where the image of the first object to be observed, which is being illuminated with the second blue light BS, the green light G, and the red light R simultaneously emitted during the second light emission, is picked up for each frame. Accordingly, during the second image pickup, B2m image signals are output from the B pixels of the image pickup sensor 48, G2m image signals are output from the G pixels, and R2m image signals are output from the R pixels.

The B1m image signals, the G1m image signals, and the R1m image signals and the B2m image signals, the G2m image signals, and the R2m image signals correspond to the first spectral images of the invention. Accordingly, the plurality of first spectral images include the B1m image signals, the G1m image signals, and the R1m image signals and the B2m image signals, the G2m image signals, and the R2m image signals.

In the reference value calculation mode, the light source control unit 42 and the image pickup control unit 55 function in the same manners as those in the ischemia evaluation mode. Accordingly, in the reference value calculation mode, the light source control unit 42 alternately performs first light emission where the BS-LED 41*a*, the G-LED 41*c*, and the R-LED 41*d* are simultaneously turned on to simultaneously emit the first blue light BS, the green light G, and the red light R and second light emission where the BL-LED 41*b*, the G-LED 41*c*, and the R-LED 41*d* are simultaneously turned on to simultaneously emit the second blue light BS, the green light G, and the red light R.

Further, in the reference value calculation mode, the image pickup control unit 55 makes image pickup control in the first light emission be different from the image pickup control in the second light emission. Specifically, in the first light emission, as shown in FIG. 8, the image pickup control unit 55 performs first image pickup where the image of the second object to be observed, which is being illuminated with the first blue light BS, the green light G, and the red light R simultaneously emitted during the first light emission, is picked up for each frame. Accordingly, during the first image pickup, B1n image signals are output from the B pixels of the image pickup sensor 48, G1n image signals are output from the G pixels, and R1n image signals are output from the R pixels. Further, the image pickup control unit 55 performs second image pickup where the image of the second object to be observed, which is being illuminated with the second blue light BS, the green light G, and the red light R simultaneously emitted during the second light emission, is picked up for each frame. Accordingly, during the second image pickup, B2n image signals are output from the B pixels of the image pickup sensor 48, G2n image signals are output from the G pixels, and R2n image signals are output from the R pixels.

The B1n image signals, the G1n image signals, and the R1n image signals and the B2n image signals, the G2n image signals, and the R2n image signals correspond to the second spectral images of the invention. Accordingly, the plurality of second spectral images include the B1n image signals, the G1n image signals, and the R1n image signals and the B2n image signals, the G2n image signals, and the R2n image signals.

The image pickup signals (analog signals) output from the image pickup sensor 48 are input to an A/D converter (not shown) through a scope cable. The A/D converter converts the image pickup signals (analog signals) into image signals (digital signals) corresponding to the voltage levels of the image pickup signals. The converted image signals are input to the processor device 23 for lumen through the connector part.

As shown in FIG. 3, the processor device 23 for lumen comprises a central control unit 56, an image acquisition unit 57, an image processing unit 58, and a display control unit 59. The image acquisition unit 57 comprises a digital signal processor (DSP) 61, a noise reduction section 62, and a conversion section 63. The display control unit 59 comprises a display image selection section 59*a*.

The DSP 61 performs various kinds of signal processing, such as defect correction processing, offset processing, gain correction processing, linear matrix processing, gamma conversion processing, demosaic processing, and YC conversion processing, on the received image signals. In the defect correction processing, the signals of the defective pixel of the image pickup sensor 48 are corrected. In the offset processing, dark current components are removed from the image signals subjected to the defect correction processing and an accurate zero level is set. In the gain correction processing, the signal level of the image signal is adjusted by the multiplication of the image signal, which corresponds to each color and has been subjected to the offset processing, and a specific gain. In the linear matrix processing, the color reproducibility of the image signal, which corresponds to each color and has been subjected to the gain correction processing, is improved.

In the gamma conversion processing, the brightness and chroma of each image signal subjected to the linear matrix processing are adjusted. In the demosaic processing (also referred to as isotropic processing or demosaicing), the signals of missing colors of the respective pixels are generated to interpolate the image signals subjected to the gamma conversion processing. All pixels are caused to have signals corresponding to the respective colors of R, G, and B by this demosaic processing. The DSP 61 performs YC conversion processing, which converts image signals into luminance signals Y and color difference signals Cb and Cr, on the respective image signals subjected to the demosaic processing, and outputs these image signals to the noise reduction section 62.

The noise reduction section 62 performs noise reduction processing on the image signals output from the DSP 61. The noise reduction processing is, for example, a moving-average method, median filtering, or the like. The image signals from which noises are removed by the noise reduction processing are input to the conversion section 63. The conversion section 63 reconvert the luminance signals Y and the color difference signals Cb and Cr, which have been subjected to the noise reduction processing, into images corresponding to the respective colors of B, G, and R.

The central control unit 56 controls the light source control unit 42 and the image pickup control unit 55 to execute each of three modes, that is, the normal mode, the ischemia evaluation mode, and the reference value calculation mode. The central control unit 56 is electrically connected to the image processing unit 58, and notifies the image processing unit 58 of whether or not one of the normal mode, the ischemia evaluation mode, or the reference value calculation mode is executed.

The central control unit 56 picks up a normal image in the normal mode. In the pickup of a normal image, the central control unit 56 controls the light source control unit 42 to cause illumination light for a normal image to be emitted. Accordingly, the image of an object to be observed illuminated with the first blue light BS, the green light G, and the red light R is picked up at the time of pickup of a normal image, so that the Bc image signals, the Gc image signals, and the Rc image signals are obtained.

Further, in the ischemia evaluation mode, the central control unit 56 controls the light source control unit 42 to cause the light source control unit 42 to alternately emit the illumination light of the first light emission and the illumination light of the second light emission and controls the image pickup control unit 55 according to the first light emission and the second light emission to cause the image pickup control unit 55 to alternately perform the first image pickup and the second image pickup. Accordingly, in a case where the first light emission and the first image pickup are performed, the image of the first object to be observed illuminated with the first blue light BS, the green light G, and the red light R is picked up, so that the B1m image signals, the G1m image signals, and the R1m image signals are obtained. Further, in a case where the second light emission and the second image pickup p are performed, the image of the first object to be observed illuminated with the second blue light BS, the green light G, and the red light R is picked up, so that the B2m image signals, the G2m image signals, and the R2m image signals are obtained. The B1m image signals, the G1m image signals, and the R1m image signals, and the B2m image signals, the G2m image signals, and the R2m image signals are two sets of consecutive image signals.

Furthermore, in the reference value calculation mode, as in the ischemia evaluation mode, the central control unit 56 controls the light source control unit 42 to cause the light source control unit 42 to alternately emit the illumination light of the first light emission and the illumination light of the second light emission and controls the image pickup control unit 55 according to the first light emission and the second light emission to cause the image pickup control unit 55 to alternately perform the first image pickup and the second image pickup. Accordingly, in a case where the first light emission and the first image pickup are performed, the image of the second object to be observed illuminated with the first blue light BS, the green light G, and the red light R is picked up, so that the B1n image signals, the G1n image signals, and the R1n image signals are obtained. Further, in a case where the second light emission and the second image pickup p are performed, the image of the second object to be observed illuminated with the second blue light BS, the green light G, and the red light R is picked up, so that the B2n image signals, the G2n image signals, and the R2n image signals are obtained. The B1n image signals, the G1n image signals, and the R1n image signals, and the B2n image signals, the G2n image signals, and the R2n image signals are two sets of consecutive image signals.

Figure 9:
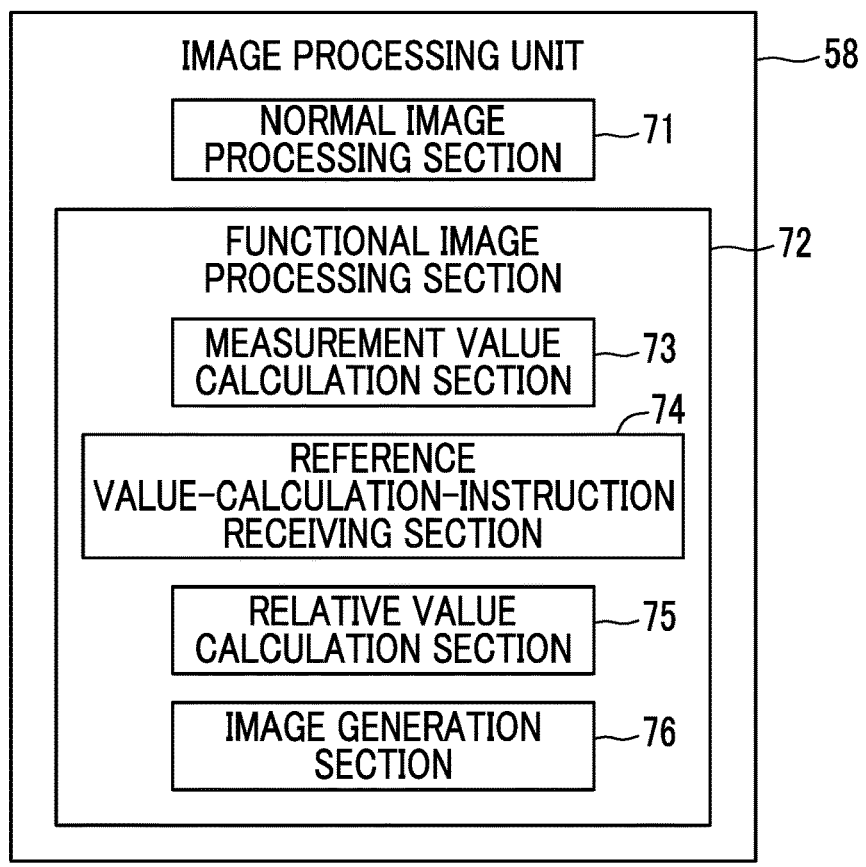
FIG. 9 is a block diagram showing the functions of an image processing unit.

As shown in FIG. 9, the image processing unit 58 comprises a normal image processing section 71 and a functional image processing section 72 and performs predetermined image processing on the image signals input from the endoscope device 22 for lumen. The normal image processing section 71 generates a normal image by performing predetermined image processing on the image signals obtained in the normal mode.

The functional image processing section 72 processes an image that is obtained in the ischemia evaluation mode or the reference value calculation mode. The functional image processing section 72 comprises a measurement value calculation section 73, a reference value-calculation-instruction receiving section 74, a relative value calculation section 75, and an image generation section 76. The functional image processing section 72 performs a series of processing on the basis of the image signals input from the endoscope device 22 for lumen, calculates the relative value of a hemoglobin concentration and the relative value of an oxygen saturation, and generates a relative value image using the relative value of a hemoglobin concentration and/or the relative value of an oxygen saturation.

The measurement value calculation section 73 has a function to calculate the actual measurement values or the reference values of a hemoglobin concentration and an oxygen saturation on the basis of a plurality of spectral images. In a case where the spectral images are the first spectral images, the calculated values of a hemoglobin concentration and an oxygen saturation are set as first actual measurement values. In a case where the spectral images are the second spectral images, the calculated values of a hemoglobin concentration and an oxygen saturation are set as second actual measurement values. Accordingly, the value of a hemoglobin concentration calculated on the basis of the plurality of first spectral images is the first actual measurement value of a hemoglobin concentration, and the value of an oxygen saturation calculated on the basis of the plurality of first spectral images is the first actual measurement value of an oxygen saturation. Further, the value of a hemoglobin concentration calculated on the basis of the plurality of second spectral images is the second actual measurement value of a hemoglobin concentration, and the value of an oxygen saturation calculated on the basis of the plurality of second spectral images is the second actual measurement value of an oxygen saturation. The reference values are calculated using the second actual measurement values.

The reference value-calculation-instruction receiving section 74 receives an instruction to calculate a reference value. The relative value calculation section 75 calculates the relative value of the concentration of hemoglobin and the relative value of the oxygen saturation of hemoglobin on the basis of the first actual measurement value of a hemoglobin concentration, the first actual measurement value of an oxygen saturation, the reference value of a hemoglobin concentration, and the reference value of an oxygen saturation that are calculated by the measurement value calculation section 73. The image generation section 76 generates a relative value image that is obtained from the imaging of the relative value of the concentration of hemoglobin and/or the relative value of the oxygen saturation of hemoglobin.

Figure 10:
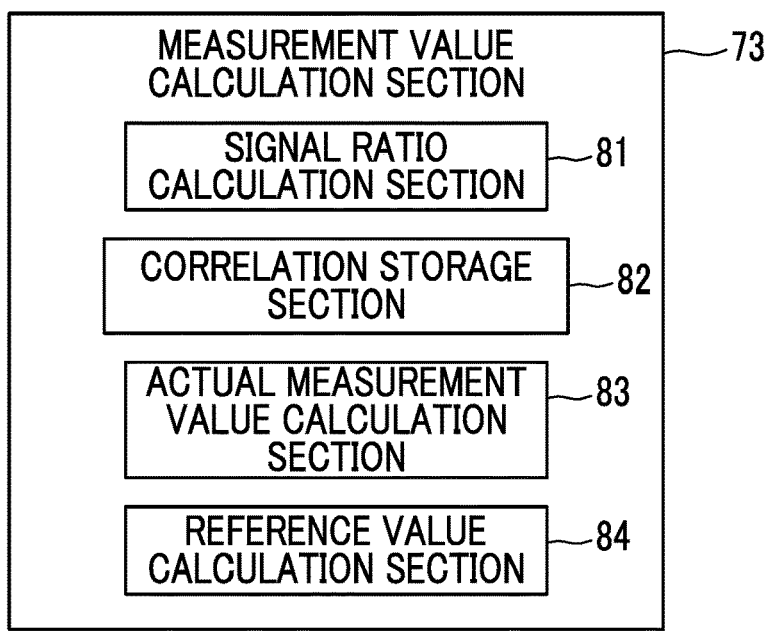
FIG. 10 is a block diagram showing the functions of a measurement value calculation section.

As shown in FIG. 10, the measurement value calculation section 73 comprises a signal ratio calculation section 81, a correlation storage section 82, an actual measurement value calculation section 83, and a reference value calculation section 84. The signal ratio calculation section 81, the correlation storage section 82, and the actual measurement value calculation section 83 calculate the first actual measurement values of a hemoglobin concentration and an oxygen saturation on the basis of the plurality of first spectral images, and calculate the second actual measurement values of a hemoglobin concentration and an oxygen saturation on the basis of the plurality of second spectral images. The reference value calculation section 84 calculates the reference values from the second actual measurement values.

The signal ratio calculation section 81 obtains signal ratios, which are dependent on both a hemoglobin concentration and an oxygen saturation, using the plurality of first spectral images that are acquired in the ischemia evaluation mode and are obtained from the image pickup of a first object to be observed including a lesion. A signal ratio dependent on a hemoglobin concentration is the same as a signal ratio dependent on the amount of blood.

The signal ratio calculation section 81 calculates signal ratios between pixels present at the same positions in the B1m image signals, the G1m image signals, and the R1m image signals of the first image pickup and the B2m image signals, the G2m image signals, and the R2m image signals of the second image pickup that are the first spectral image acquired in the ischemia evaluation mode. The signal ratios are calculated for all pixels of the image signals. Accordingly, a hemoglobin concentration and an oxygen saturation are calculated for each pixel. In this embodiment, the signal ratio calculation section 81 obtains a signal ratio B2m/(B1m+G1m) of the B2m image signal of the second image pickup to the B1m image signal of the first image pickup and the G1m image signal of the first image pickup and a signal ratio R1m/G1m of the R1m image signal of the first image pickup to the G1m image signal of the first image pickup. The signal ratios may be obtained for only the pixels of blood vessel portions among the image signals. In this case, the blood vessel portions are specified on the basis of differences between the image signals of blood vessel portions and the image signals of other portions.

Figure 11:
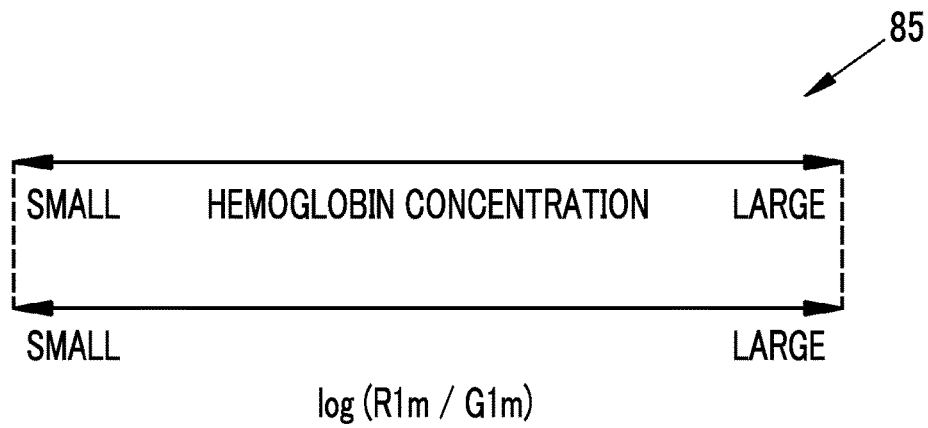
FIG. 11 is a graph showing a correlation between a hemoglobin concentration and a signal ratio.

The correlation storage section 82 stores a correlation between the signal ratio B2m/(B1m+G1m) and the signal ratio R1m/G1m and a hemoglobin concentration and an oxygen saturation. As shown in FIG. 11, the correlation between the signal ratio and a hemoglobin concentration is stored as a one-dimensional table defined so that a hemoglobin concentration is also increased as the signal ratio R1m/G1m is increased. The signal ratio R1m/G1m is stored on a log scale.

Figure 12:
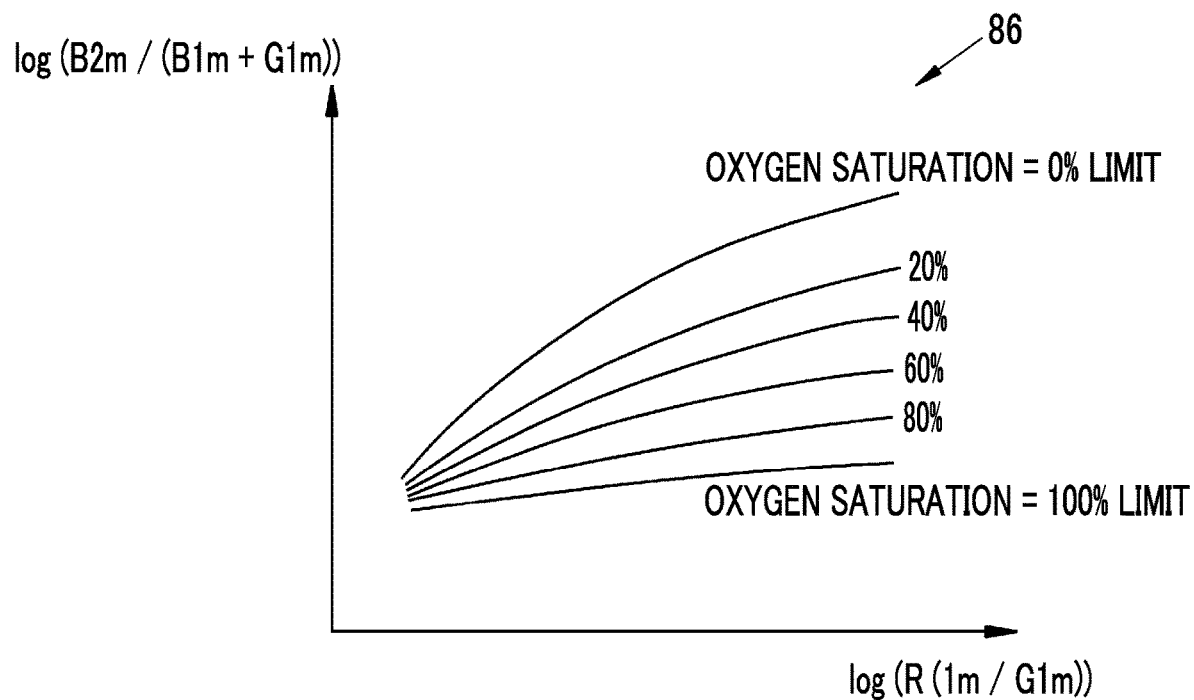
FIG. 12 is a graph showing a correlation between an oxygen saturation and a signal ratio.

On the other hand, the correlation between the signal ratio and an oxygen saturation is stored as a two-dimensional table that defines the level curves of an oxygen saturation in a two-dimensional space shown in FIG. 12. The positions and shapes of the level curves are obtained from the physical simulation of light scattering, and are defined to be changed according to the amount of blood. For example, in a case where the amount of blood is changed, an interval between the respective level curves is increased or reduced. The signal ratio B2m/(B1m+G1m) and the signal ratio R1m/G1m are stored on a log scale.

Figure 13:
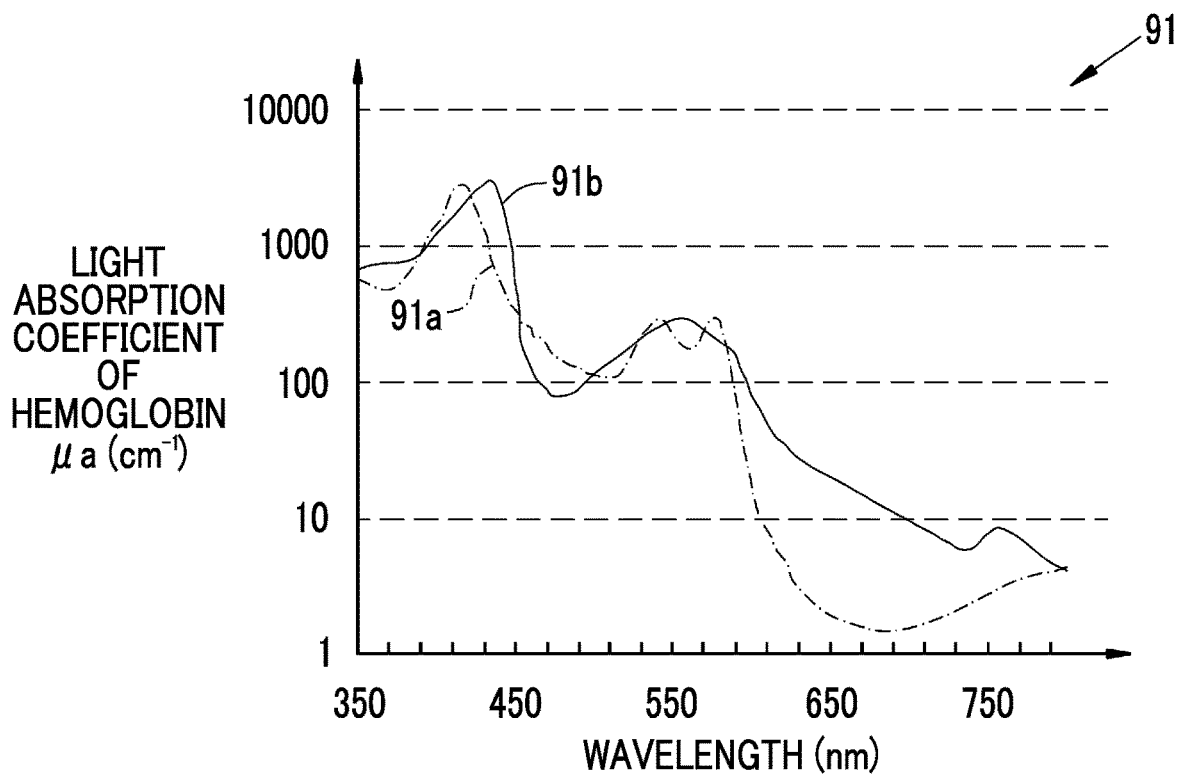
FIG. 13 is a graph showing the light absorption coefficient of hemoglobin.

The correlation is closely related to the light absorption characteristics and light scattering characteristics of oxyhemoglobin and reduced hemoglobin shown in FIG. 13. In FIG. 13, a graph 91 shows a light absorption coefficient 91a of oxyhemoglobin and a light absorption coefficient 91b of reduced hemoglobin. As shown in FIG. 13, information about an oxygen saturation is easily obtained at, for example, a wavelength where a difference in the light absorption coefficient is large, such as 470 nm. However, a blue signal, which includes a signal corresponding to a light having a wavelength of 470 nm, is highly dependent on not only an oxygen saturation but also the amount of blood. Accordingly, in a case where the signal ratio B2m/(B1m+G1m) and the signal ratio R1m/G1m obtained from the R1m image signal corresponding to light mainly changing depending on the amount of blood and the G1m image signal serving as a reference signal of the B2m image signal and R1m image signal in addition to the B1m image signal are used, an oxygen saturation can be accurately obtained without depending on the amount of blood.

Further, the following three points can be said from the wavelength dependence of the light absorption coefficient of hemoglobin of a tissue to be observed that is an object to be observed.

(1) A light absorption coefficient is significantly changed according to the change of an oxygen saturation at a wavelength close to 470 nm (for example, in a blue wavelength range having a central wavelength of 470 nm±10 nm).
(2) A light absorption coefficient is hardly affected by an oxygen saturation on average in a green wavelength range of 540 to 580 nm.
(3) In a red wavelength range of 590 to 700 nm, a light absorption coefficient seems to be significantly changed at first glance depending on an oxygen saturation but the value of a light absorption coefficient itself is very small. As a result, a light absorption coefficient is hardly affected by an oxygen saturation.

The actual measurement value calculation section 83 obtains both a hemoglobin concentration and an oxygen saturation at each pixel using the correlation that is stored in the correlation storage section 82 and the signal ratio B2m/(B1m+G1m) and the signal ratio R1m/G1m that are obtained by the signal ratio calculation section 81. In regard to a hemoglobin concentration, a value in the one-dimensional table of the correlation storage section 82, which corresponds to the signal ratio R1m/G1m obtained by the signal ratio calculation section 81, is a hemoglobin concentration. On the other hand, in regard to an oxygen saturation, as shown in FIG. 14, a corresponding point P, which corresponds to a signal ratio B2m*/(B1m*+G1m*) and a signal ratio R1m*/G1m* obtained by the signal ratio calculation section 81, is specified first in the two-dimensional space.

Figure 14:
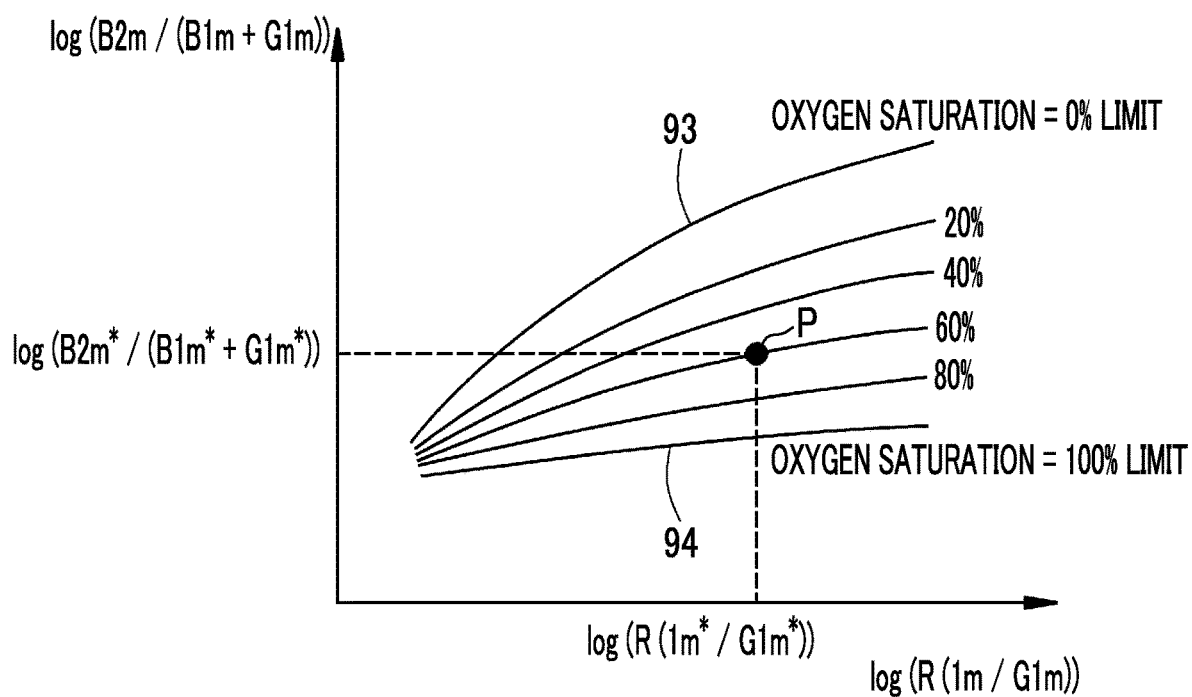
FIG. 14 is a diagram illustrating a method of obtaining the actual measurement value of an oxygen saturation from a signal ratio in a graph 86.

Then, in a case where the corresponding point P is positioned between a lower limit line 93 of "oxygen saturation=0% limit" and an upper limit line 94 of "oxygen saturation=100% limit" as shown in FIG. 14, a percentage value indicated by a level curve on which the corresponding point P is positioned is an oxygen saturation. For example, since the level curve on which the corresponding point P is positioned indicates 60% in the case of FIG. 14, 60% is an oxygen saturation. In a case where the corresponding point is positioned outside a region between the lower limit line 93 and the upper limit line 94, an oxygen saturation is set to 0% in a case where the corresponding point is positioned above the lower limit line 93 and an oxygen saturation is set to 100% in a case where the corresponding point is positioned below the upper limit line 94. In a case where the corresponding point is positioned outside a region between the lower limit line 93 and the upper limit line 94, the reliability of an oxygen saturation at the pixel thereof may be displayed without being reduced.

Next, the calculation of the reference values of a hemoglobin concentration and an oxygen saturation for the plurality of second spectral images will be described. After the reference value-calculation-instruction receiving section 74 receives an operator's instruction and a mode is switched to the reference value calculation mode, the calculation of a reference value is started. For example, the operator's instruction is, specifically, the press of a scope button that is the reference value-calculation-instruction part 28b. In a case where an operator presses the scope button, which is the reference value-calculation-instruction part 28b, on, for example, an object to be observed desired to be set to a reference value during the examination, a mode is switched to the reference value calculation mode and the plurality of second spectral images obtained from the image pickup of this object to be observed are acquired.

The second actual measurement values of a hemoglobin concentration and an oxygen saturation at each pixel are obtained using the plurality of acquired second spectral images by the same processing as the processing for calculating the first actual measurement values. More specifically, the signal ratio calculation section 81 obtains signal ratios, which are dependent on both a hemoglobin concentration and an oxygen saturation, using the plurality of second spectral images that are obtained on the basis of the operation of the reference value-calculation-instruction part 28b. A signal ratio based on the second spectral images is the second actual measurement value of the oxygen saturation of the second object to be observed. Specifically, the second actual measurement values are obtained from the plurality of second spectral images using the signal ratio B2n/(B1n+G1n) and the signal ratio R1n/G1n that are calculated by the signal ratio calculation section 81 and the correlation and the two-dimensional space (see FIG. 14) that are stored in the correlation storage section 82. Since the calculation of a hemoglobin concentration is based on the signal ratio R1n/G1n as in the case of the first actual measurement value even in regard to the second actual measurement value of the hemoglobin concentration of the second object to be observed, the calculation of a hemoglobin concentration is performed for each pixel of these spectral images.

The reference value calculation section 84 averages the second actual measurement values of a hemoglobin concentration and an oxygen saturation at the respective pixels, which are calculated by the actual measurement value calculation section 83, in, for example, the range of one image, the range of one spectral image, or the like, respectively. The value, which is averaged and calculated, is set as the reference value of a hemoglobin concentration or the reference value of an oxygen saturation. In the case of averaging, the weight of reliability at each pixel may be weighted and averaged so that the value of an inappropriate region is not included due to the calculation of a reference value. After the reference value is calculated, the calculated reference value is sent to the relative value calculation section 75 and the relative value calculation section 75 calculates a relative value using the calculated reference value.

The reference value calculation section 84 may calculate the reference value using a plurality of sets of a plurality of second spectral images. In this case, for example, one set of spectral images is used as one frame, the average value of the oxygen saturation of each frame is obtained, the obtained average value is further added, and the resultant value is divided by the number of frames to obtain the reference value of an oxygen saturation of all the plurality of frames. Even in regard to the first actual measurement values of a hemoglobin concentration and an oxygen saturation based on the first spectral images, the average values for the pixel of the same position may be obtained from a plurality of frames and may be used as the first actual measurement values of a hemoglobin concentration and an oxygen saturation.

The switching of a mode to the reference value calculation mode or the calculation of the reference value may be performed by a method other than a method that is started according to an operator's instruction. Further, for example, at the beginning of an operation, the typical value of a hemoglobin concentration or an oxygen saturation indicated by the normal mucous membrane of a digestive tract from the mouth to the anus may be set as a default reference value in advance. Furthermore, a reference value up to the previous time may be stored, and the reference value may be used until an operator gives an instruction to calculate a reference value and may be updated in a case where an operator gives an instruction to calculate a reference value. Moreover, in a case where a mode is switched to the ischemia evaluation mode by the mode switching part 28a, a mode may be automatically switched to the reference value calculation mode once, the reference value may be calculated, and a mode may be automatically switched to the ischemia evaluation mode after the reference value is set.

Figure 15:
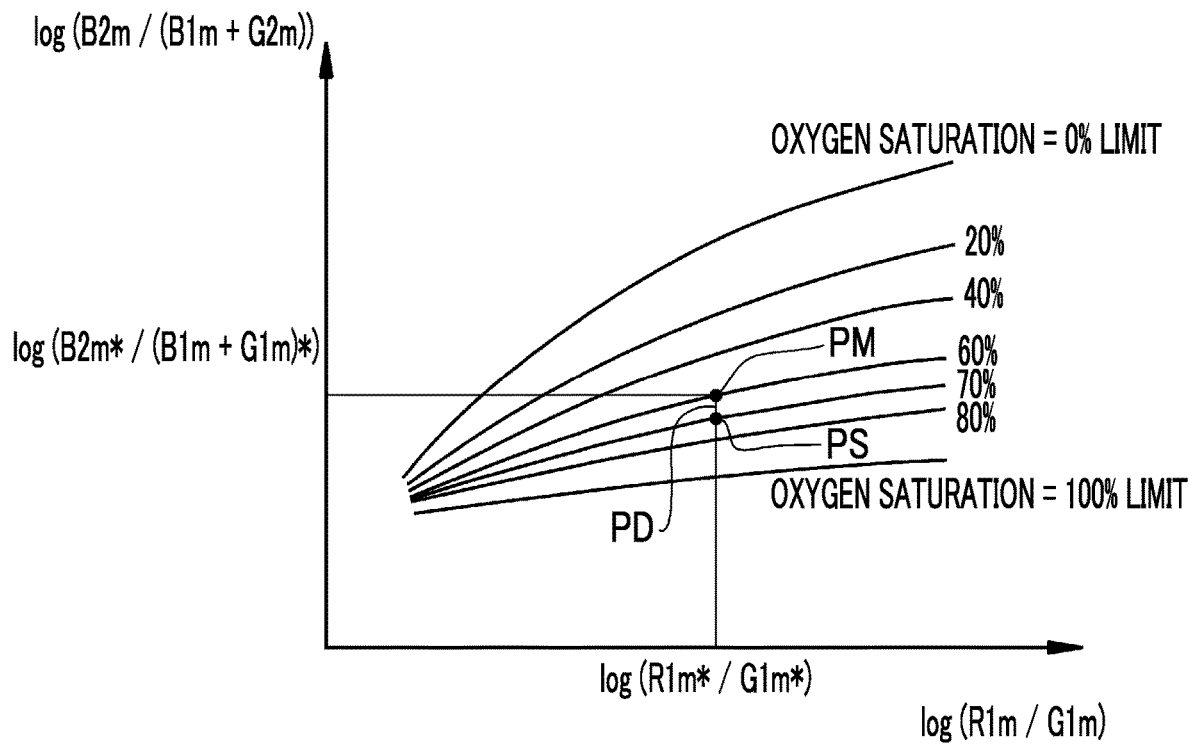
FIG. 15 is a diagram illustrating a method of obtaining the relative value of an oxygen saturation from a signal ratio in the graph 86.

The relative value calculation section 75 calculates the relative values of a hemoglobin concentration and an oxygen saturation, which are based on the first spectral images, on the basis of the first actual measurement values of a hemoglobin concentration and an oxygen saturation based on the first spectral images and the reference values of a hemoglobin concentration and an oxygen saturation. For example, the relative value can be a value that is obtained by subtracting the reference value from the first actual measurement value. Specifically, in a case where the first actual measurement value of an oxygen saturation based on the first spectral images is denoted by $StO_2(MV)$ and the reference value of an oxygen saturation is denoted by $StO_2(STD)$, the relative value $\Delta StO$ of an oxygen saturation is a value that is obtained by subtracting the reference value $StO_2(STD)$ of an oxygen saturation from the first actual measurement value $StO_2(MV)$ of an oxygen saturation. Accordingly, the relative value $\Delta StO_2$ of an oxygen saturation is, for example, a difference PD in a case where the reference value PS of an oxygen saturation and the first actual measurement value PM of an oxygen saturation are set as shown in FIG. 15. In a case where the relative value $\Delta StO_2$ of an oxygen saturation is represented by Equation, the following is obtained.

$$StO_2(MV) - StO_2(STD) = \Delta StO_2$$

Figure 16:
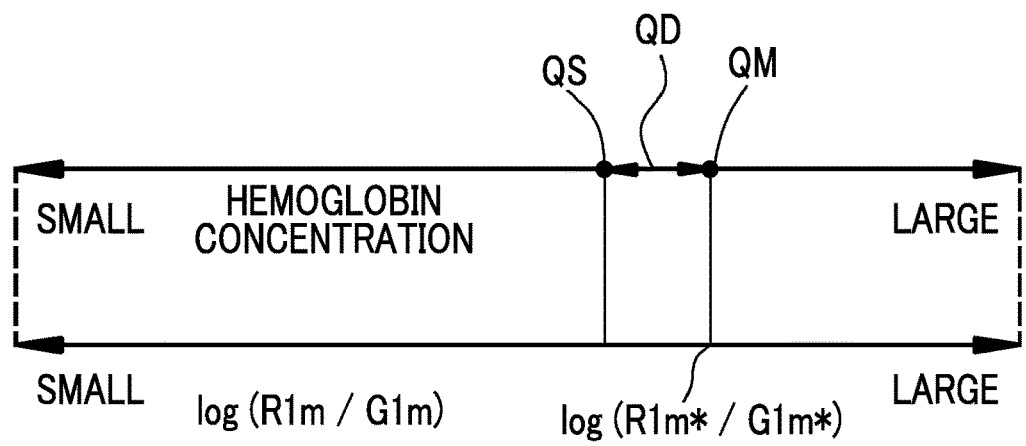
FIG. 16 is a diagram illustrating a method of obtaining the relative value of a hemoglobin concentration from a signal ratio in a graph 85.

The relative value of a hemoglobin concentration is also calculated in the same manner as the relative value of an oxygen saturation. That is, the relative value can be a value that is obtained by subtracting the reference value from the first actual measurement value. Specifically, in a case where the first actual measurement value of a hemoglobin concentration based on the first spectral images is denoted by cHb(MV) and the reference value of a hemoglobin concentration is denoted by cHb(STD), the relative value $\Delta cHb$ of a hemoglobin concentration is a value that is obtained by subtracting the reference value cHb(STD) of a hemoglobin concentration from the first actual measurement value cHb(MV) of a hemoglobin concentration. Accordingly, the relative value $\Delta cHb$ of a hemoglobin concentration is, for example, a difference QD in a case where the reference value QS of a hemoglobin concentration and the actual measurement value QM of an oxygen saturation are set as shown in FIG. 16. In a case where the relative value $\Delta StO_2$ of an oxygen saturation is represented by Equation, the following is obtained.

cHb(MV)−cHb(STD)=ΔcHb

Next, the image generation section 76 generates a relative value image that is obtained from the imaging of the relative value ΔcHb of a hemoglobin concentration and/or the relative value $\Delta StO_2$ of an oxygen saturation obtained by the relative value calculation section 75. Specifically, the image generation section 76 generates a hemoglobin concentration image by converting the relative value ΔcHb of a concentration into a pseudo-color image using a color table for concentration that stores pseudo-color information changing according to a concentration, and generates an oxygen saturation image by converting the relative value $\Delta StO_2$ of an oxygen saturation into a pseudo-color image using a color table for an oxygen saturation that stores pseudo-color information changing according to an oxygen saturation. The relative value image includes the hemoglobin concentration image that is obtained from the imaging of the relative value ΔcHb of a hemoglobin concentration, the oxygen saturation image that is obtained from the imaging of the relative value $\Delta StO_2$ of an oxygen saturation, and a determination index image that is obtained from the imaging of the relative value ΔcHb of a hemoglobin concentration and the relative value $\Delta StO_2$ of an oxygen saturation.

Figure 17:
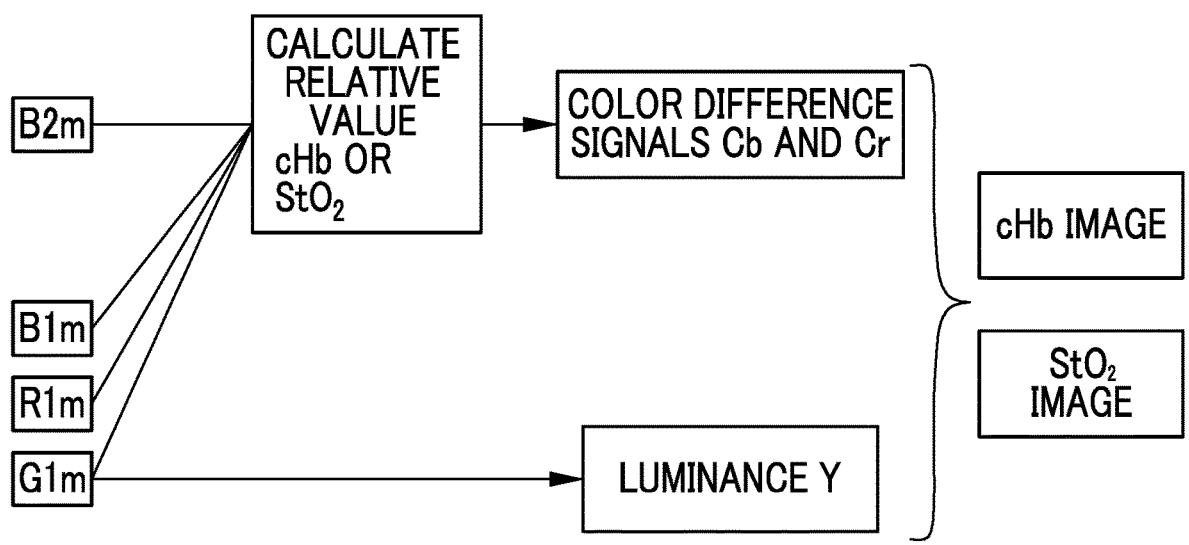
FIG. 17 is a block diagram showing a procedure for generating a hemoglobin concentration image and an oxygen saturation image.

As shown in FIG. 17, the image generation section 76 generates a hemoglobin concentration image representing the relative value ΔcHb of a hemoglobin concentration, which is obtained by the relative value calculation section 75, with a pseudo color. The hemoglobin concentration image is composed of video signals that are formed of luminance Y and color difference signals Cb and Cr. The G1m image signal of a green signal is assigned to the luminance Y. Since the G1m image signal corresponds to reflected light having a wavelength range where the absorption of light by hemoglobin is somewhat strong, the unevenness of a mucous membrane, blood vessels, and the like can be visually recognized from an image based on the G1m image signal. Accordingly, since the G1m image signal is assigned to the luminance, the overall brightness of the pseudo-color image can be defined. The G2m image signal of a green signal may be assigned to the luminance instead of the G1m image signal.

Figure 18:
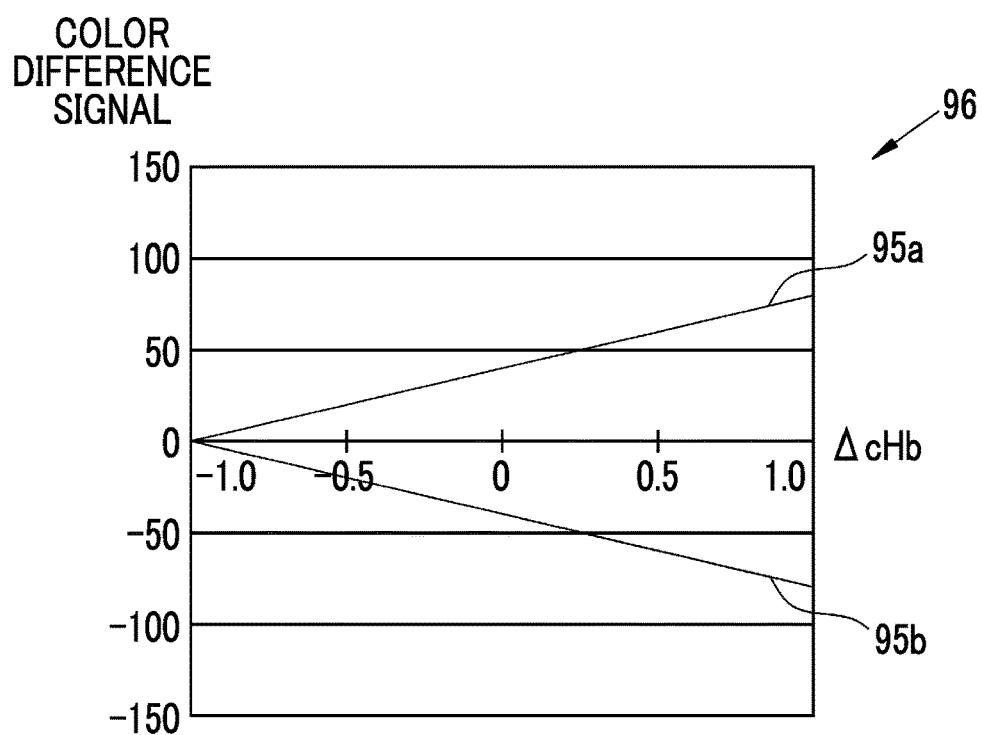
FIG. 18 is a graph showing a relationship between the relative value of a hemoglobin concentration and a color difference signal.

On the other hand, as shown in FIG. 18, signal values corresponding to the relative value ΔcHb of a hemoglobin concentration are assigned to the color difference signals Cb and Cr according to a color table 96. The color table 96 is a color table for a hemoglobin concentration image that stores pseudo-color information changing according to a hemoglobin concentration. The color table 96 is defined so that the signal value of a color difference signal Cb 95b is reduced with an increase in a hemoglobin concentration and the signal value of a color difference signal Cr 95a is increased with an increase in a hemoglobin concentration. Accordingly, redness is increased at a position in the hemoglobin concentration image where a hemoglobin concentration is increased, and the chroma of redness is reduced with a reduction in a hemoglobin concentration, so that the hemoglobin concentration image approaches monochrome.

Figure 19:
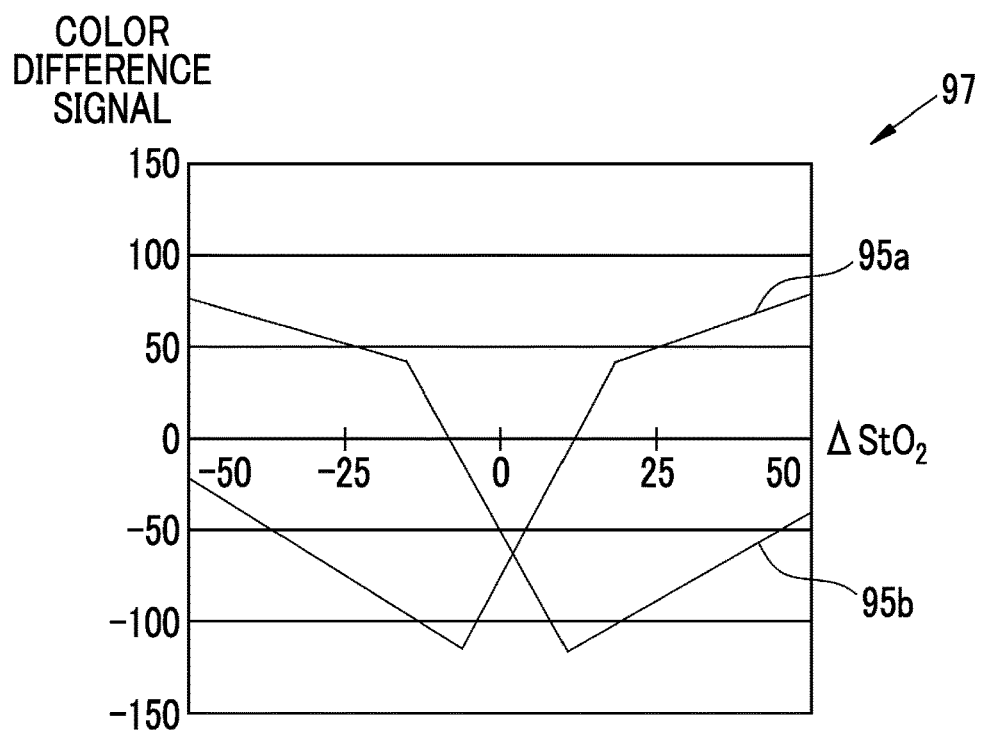
FIG. 19 is a graph showing a relationship between the relative value of an oxygen saturation and a color difference signal.

As shown in FIG. 17, the image generation section 76 generates an oxygen saturation image representing the relative value $\Delta StO_2$ of an oxygen saturation, which is obtained by the relative value calculation section 75, with a pseudo color. Like the hemoglobin concentration image, the oxygen saturation image is composed of video signals that are formed of luminance Y and color difference signals Cb and Cr. The G1m image signal of a green signal or the G2m image signal of a green signal is assigned to the luminance Y. As shown in FIG. 19, signal values corresponding to the relative value $\Delta StO_2$ of an oxygen saturation are assigned to the color difference signals Cb and Cr according to a color table 97. The color table 97 is a color table for an oxygen saturation image that stores pseudo-color information changing according to an oxygen saturation.

The color table 97 is defined so that the signal value of a color difference signal Cr 95a is positive and the signal value of a color difference signal Cb 95b is negative under a high oxygen saturation, and, conversely, the signal value of a color difference signal Cr 95a is negative and the signal value of a color difference signal Cb 95b is positive under a low oxygen saturation. Further, the color table 97 is defined so that a magnitude relationship between the signal value of a color difference signal Cr 95a and the signal value of a color difference signal Cb 95b is reversed under a medium oxygen saturation. Accordingly, the tint of the oxygen saturation image is changed in the order of a blue color, a light blue color, a green color, a yellow color, an orange color, and a red color toward a high oxygen saturation from a low oxygen saturation.

Figure 20:
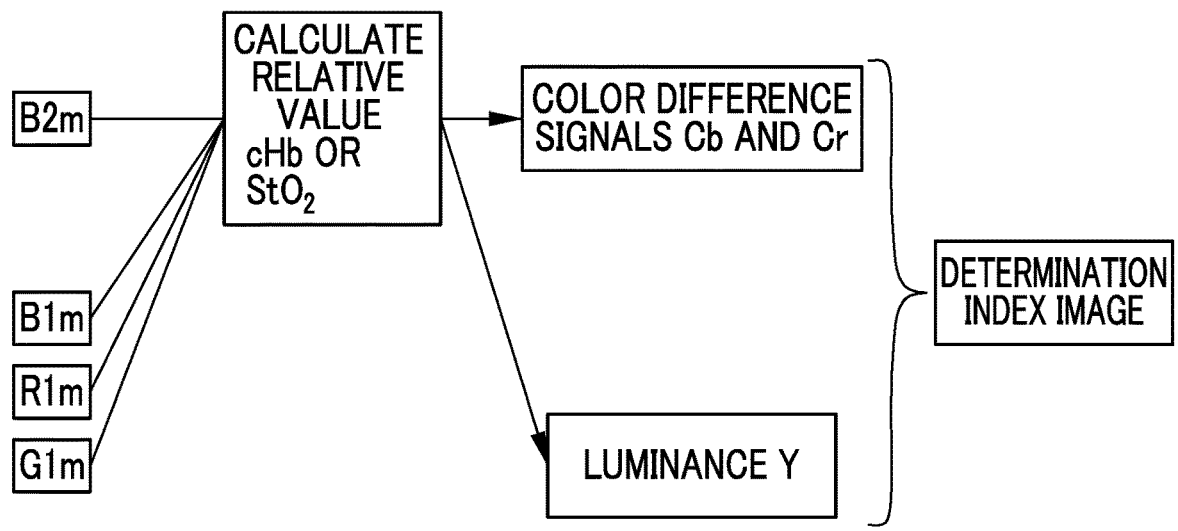
FIG. 20 is a block diagram showing a procedure for generating a relative value image.

Further, as shown in FIG. 20, the image generation section 76 generates a determination index image representing the relative value ΔcHb of a hemoglobin concentration and the relative value $\Delta StO_2$ of an oxygen saturation, which are obtained by the relative value calculation section 75, with pseudo colors. Like the hemoglobin concentration image or an oxygen saturation image, the determination index image is composed of video signals that are formed of luminance Y and color difference signals Cb and Cr.

Figure 21:
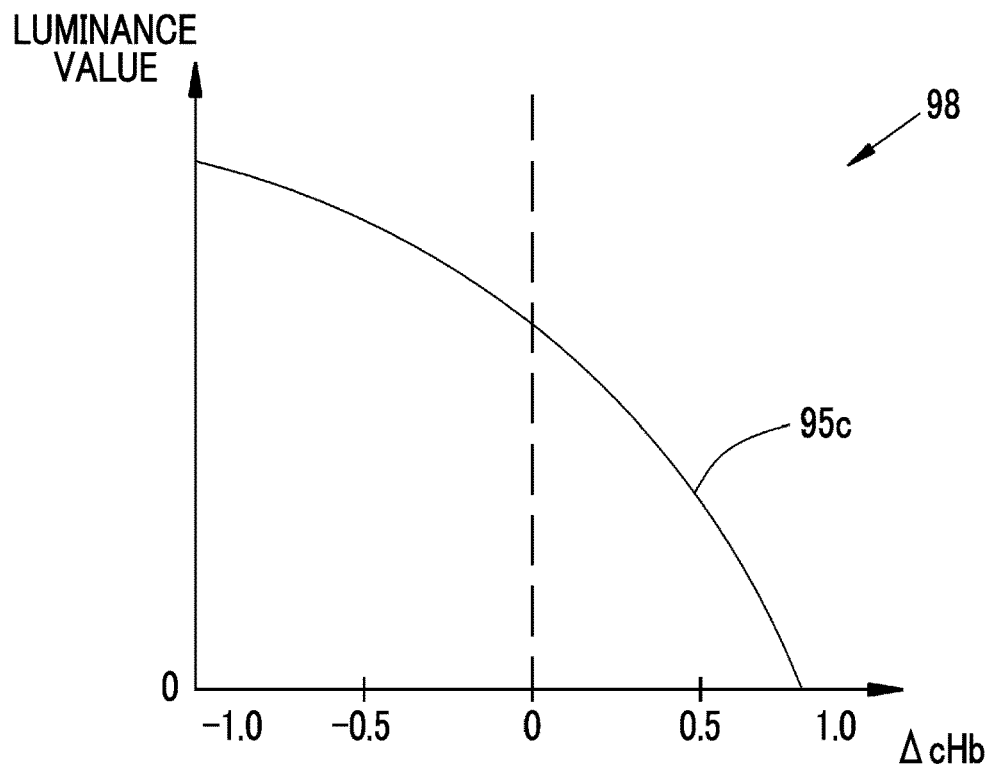
FIG. 21 is a graph showing a relationship between the relative value of a hemoglobin concentration for a determination index image and a luminance signal.
Figure 22:
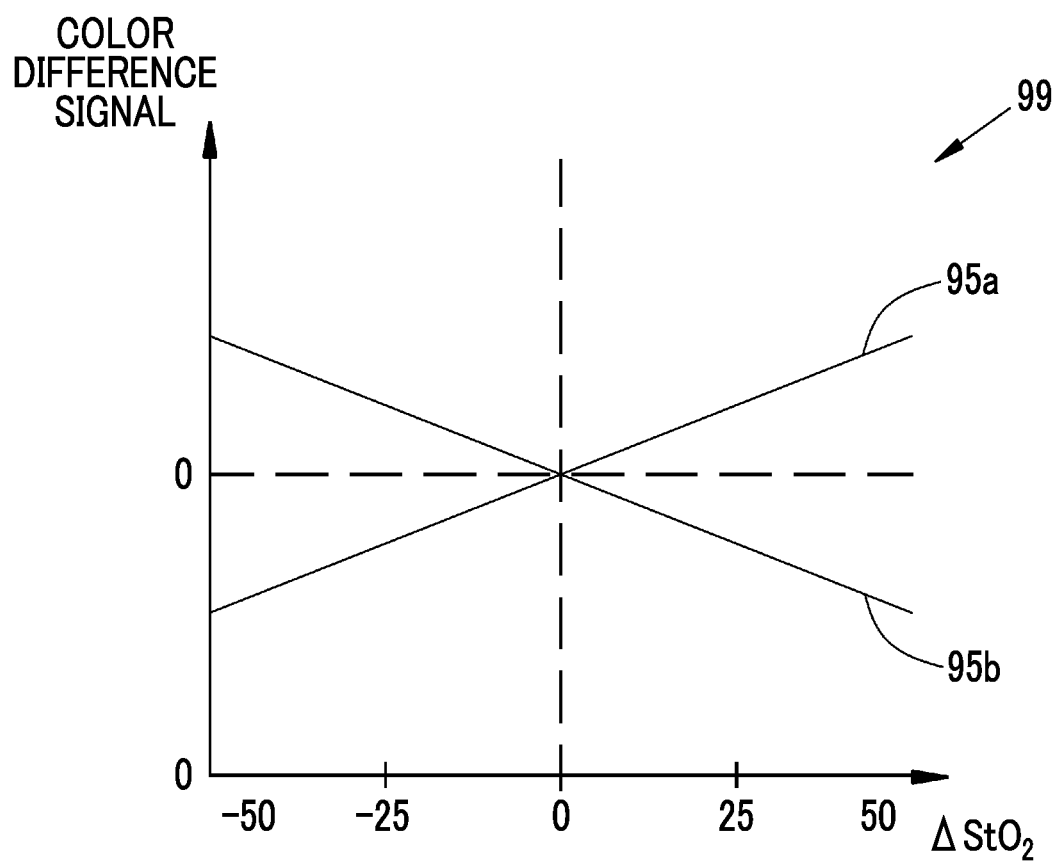
FIG. 22 is a graph showing a relationship between the relative value of an oxygen saturation for a determination index image and a color difference signal.

As shown in FIG. 21, a luminance value 95c corresponding to the relative value ΔcHb of a hemoglobin concentration is assigned to the luminance Y according to a luminance table 98. The luminance table 98 is a color table for a determination index image that stores luminance information changing according to the relative value ΔcHb of a hemoglobin concentration. As shown in FIG. 22, signal values corresponding to the relative value $\Delta StO_2$ of an oxygen saturation are assigned to the color difference signals Cb and Cr according to a color table 99. The color table 99 is a color table for a determination index image that stores pseudo-color information changing according to the relative value $\Delta StO_2$ of an oxygen saturation.

The luminance table 98 is defined so that the luminance value 95c is a small positive value at a position where the relative value ΔcHb of a hemoglobin concentration is a large positive value, conversely, the luminance value 95c is a large positive value at a position where the relative value ΔcHb of a hemoglobin concentration is a negative value having a large absolute value, and the luminance value 95c is medium at a position where the relative value ΔcHb of a hemoglobin concentration is 0 (zero). Accordingly, as the relative value ΔcHb of a hemoglobin concentration is changed to a positive value having a large absolute value from a negative value having a large absolute value, an image is displayed with a change in luminance to low luminance from high luminance.

The color table 99 is defined so that the signal value of a color difference signal Cr 95a is a large positive value and the signal value of a color difference signal Cb 95b is a negative value having a large absolute value at a position where the relative value $\Delta StO_2$ of an oxygen saturation is a large positive value. On the other hand, the color table 99 is defined so that, conversely, the signal value of a color difference signal Cr 95a is a negative value having a large absolute value and the signal value of a color difference signal Cb 95b is a large positive value at a position where the relative value $\Delta StO_2$ of an oxygen saturation is a negative value having a large absolute value and the signal value of a color difference signal Cr 95a is 0 (zero) and the signal value of a color difference signal Cb 95b is 0 (zero) at a position where the relative value $\Delta cHb$ of a hemoglobin concentration is 0 (zero). Accordingly, as the relative value $\Delta StO_2$ of an oxygen saturation is changed to a large positive value from a negative value having a large absolute value, an image is displayed while being gradually changed to red from blue.

As described above, luminance and a color difference are defined in the determination index image on the basis of the relative value $\Delta cHb$ of a hemoglobin concentration and the relative value $\Delta StO_2$ of an oxygen saturation. Accordingly, a region where the amount of blood is large is displayed to be dark, a region where the amount of blood is small is displayed to be bright, a region where the relative value $\Delta StO_2$ of an oxygen saturation is large is displayed with a red tone, and a region where the relative value $\Delta StO_2$ of an oxygen saturation is small is displayed with a blue tone. A region where the relative value $\Delta StO_2$ of an oxygen saturation is 0 (zero), that is, the first actual measurement value of an oxygen saturation is equal to the reference value is displayed with a monochromatic tone. Accordingly, a region where congestion occurs (the amount of blood is large and the amount of oxygen is low) is displayed with a dark blue color, and a region where ischemia occurs (the amount of blood is small and the amount of oxygen is low) is displayed with a light blue color. Therefore, congestion and ischemia can be distinguished from a normal case and can be visually recognized by the determination index image. The definitions of luminance and a color difference are not limited to those described above. For example, a region where the amount of blood is large may be displayed to be bright and a region where the amount of blood may be small is displayed to be dark, and the definitions of luminance and a color difference may be changed in the image generation section 76 by setting.

The display control unit 59 (see FIG. 2) controls an image to be displayed on the display device 12. The display image selection section 59a displays a display image, which is selected by the input device 14 or the like, on the display device 12. For example, at least one of the hemoglobin concentration image, the oxygen saturation image, or the determination index image is selected in the ischemia evaluation mode.

Figure 23:
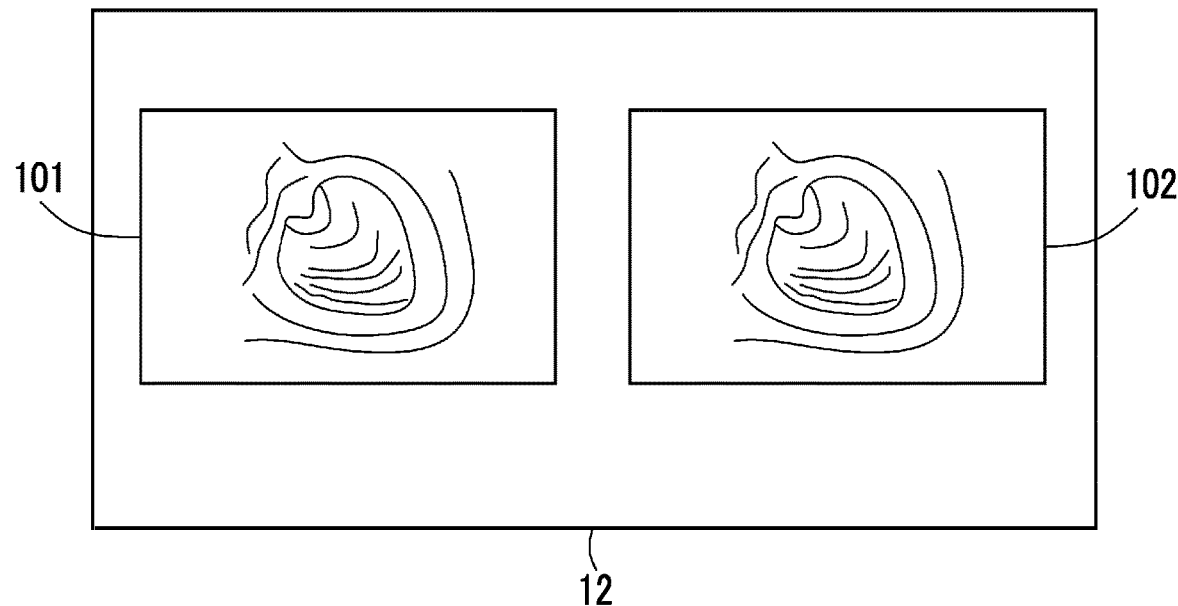
FIG. 23 is an image diagram of a display device that displays a hemoglobin concentration image and an oxygen saturation image in parallel.
Figure 24:
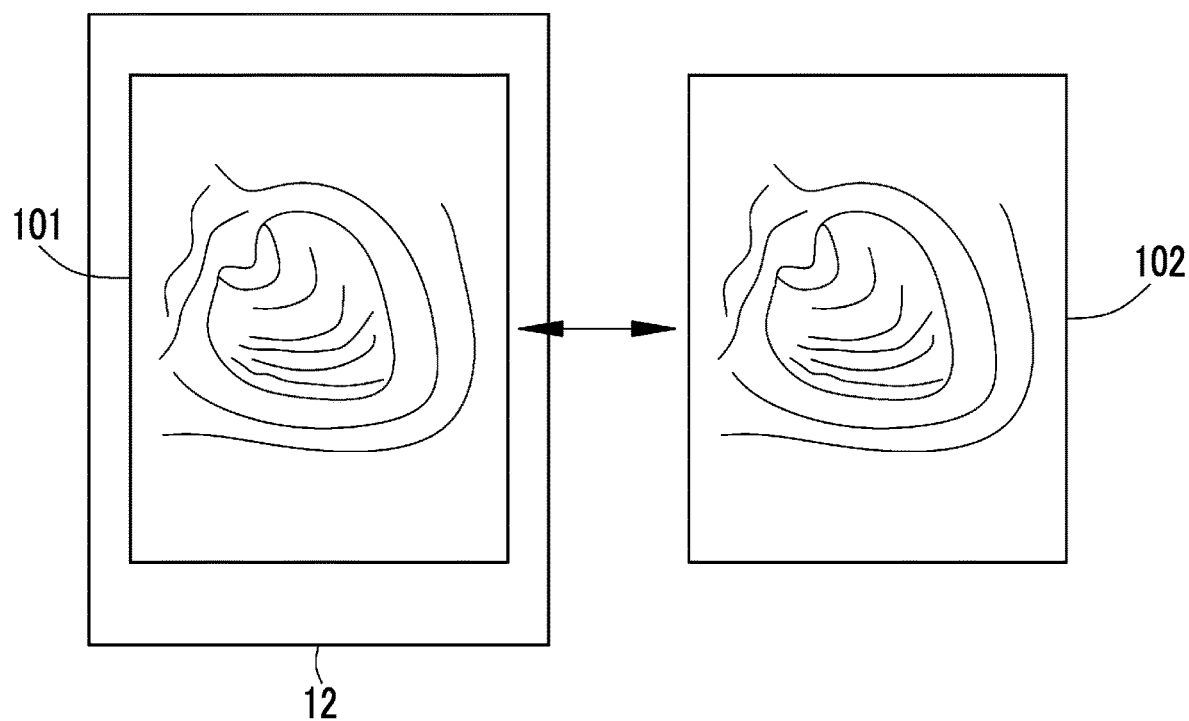
FIG. 24 is an image diagram of a display device that displays any one of a hemoglobin concentration image or an oxygen saturation image.
Figure 25:
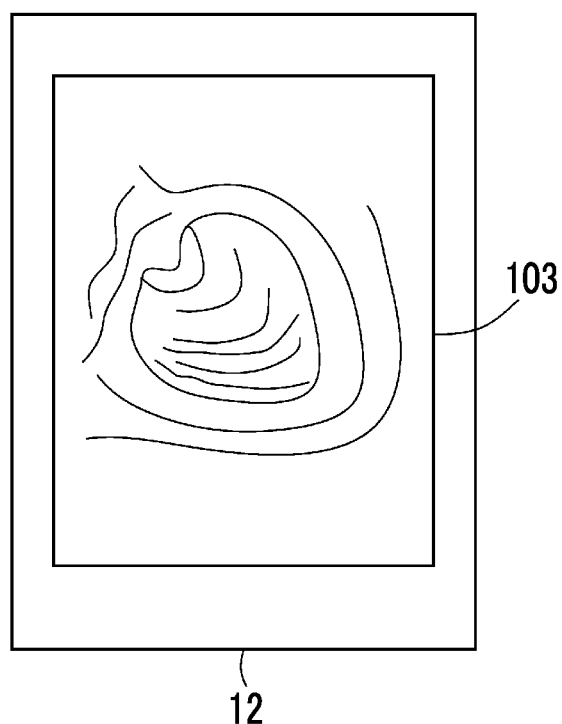
FIG. 25 is an image diagram of a display device that displays a determination index image.

A monitor, which is the display device 12, displays at least one of the hemoglobin concentration image, the oxygen saturation image, or the determination index image in, for example, the ischemia evaluation mode according to a selection received by the display image selection section 59a. A display method can be randomly set. For example, as shown in FIG. 23, a hemoglobin concentration image 101 and an oxygen saturation image 102 may be reduced in size so to be capable of being displayed on one screen in parallel and these images reduced in size may be simultaneously on the same screen of the monitor in parallel. Alternatively, as shown in FIG. 24, any one of the hemoglobin concentration image 101 and the oxygen saturation image 102 may be selected according to a selection received by the display image selection section 59a and the selected image may be displayed on the monitor while the selection is switched in some cases. Further, a determination index image 103 may be displayed on the monitor as shown in FIG. 25.

As described above, in the ischemia evaluation mode, the real-time information about both the relative value $\Delta cHb$ of a hemoglobin concentration and the relative value $\Delta StO_2$ of an oxygen saturation can be displayed by the respective images or one image. Accordingly, these relative values can be easily compared with each other by an endoscope device without the use of a fluorescent agent or the like. Further, since the hemoglobin concentration image, the oxygen saturation image, and the determination index image are images that are obtained from the imaging of the respective relative values, information about a hemoglobin concentration and an oxygen saturation can be stably obtained. Furthermore, since the distribution or boundaries of congestive regions or ischemic regions in a region where an oxygen saturation is low, the distribution or boundaries of a region where an oxygen saturation is low and a normal region, and the like can be determined, the results of the determination are useful as information for determination that is used for the prevention of the failure of the sutures after surgery. Therefore, according to the invention, it is possible to easily and stably provide a determination index for ischemia or congestion that can be used as information for the determination of a resection position or an anastomosis position where the failure of the sutures hardly occurs.

Figure 26:
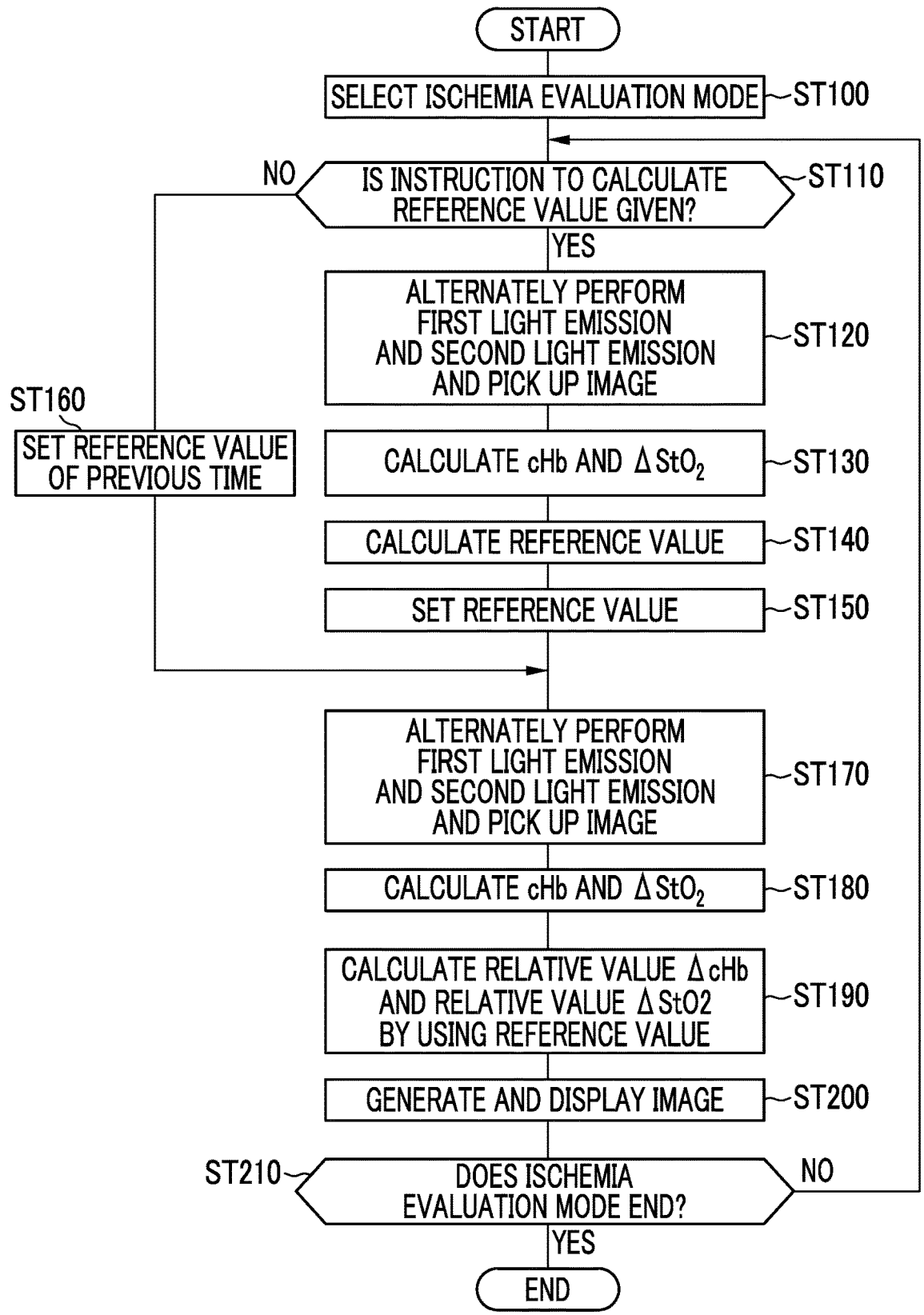
FIG. 26 is a flowchart showing the action of the invention.

Next, the action of the invention will be described with reference to a flowchart of FIG. 26. For example, in a case where the endoscope system 20 for lumen and the endoscope system 30 for abdominal cavity are used to resect the large intestine, an operator finds a portion where a tumor portion is formed in the large intestine by the endoscope device 22 for lumen that is set to the normal mode. Then, the operator inserts a clip device into the tumor portion through a forceps channel, and operates the clip device to press a relatively thick blood vessel, which is positioned close to the tumor portion, by clips. A tissue present around the blood vessel pressed by the clips is in the state of ischemia, and becomes a hypoxic region where the oxygen saturation of a tissue to be observed is lowered. This hypoxic region serves as a marker in a case where the position of the tumor portion is to be specified in the next surgery. After marking by the clips, the operator extracts the endoscope device 22 for lumen from the large intestine.

After that, in the surgery, the operator inserts the endoscope device 32 for abdominal cavity into the abdomen of the patient 40, selects the ischemia evaluation mode (Step ST100), and presses the scope button of the reference value-calculation-instruction part 28b for a normal region of the tissue as an object (YES in Step ST110). Accordingly, the mode is switched to the reference value calculation mode and an object to be observed is irradiated with the illumination light of the first light emission. The images of light and the like reflected from the object to be observed are picked up by the image pickup sensor 48 that is a color CCD including B pixels, G pixels, and R pixels. Accordingly, the image signals of the first frame formed of B1n image signals, G1n image signals, and R1n image signals are obtained. After the image signals of the first frame are obtained, the object to be observed is irradiated with the illumination light of the second light emission. The images of light and the like reflected from the object to be observed are picked up by the image pickup sensor 48, so that the image signals of the second frame formed of B2n image signals, G2n image signals, and R2n image signals are obtained (Step ST120).

After the image signals of the second frame are obtained, the signal ratio calculation section 81 obtains a signal ratio B2n/(B1n+G2n) and a signal ratio R1n/G1n at the pixel that is present at the same position between the image signals of the first frame and the image signals of the second frame. The signal ratios are obtained at all the pixels. After the signal ratios are obtained, a hemoglobin concentration corresponding to the signal ratio R1n/G1n obtained by the signal ratio calculation section 81 is obtained and an oxygen saturation corresponding to the signal ratio B2n/(B1n+G2n) and the signal ratio R1n/G1n obtained by the signal ratio calculation section 81 is obtained from the correlation stored in the correlation storage section 82. The hemoglobin concentrations and the oxygen saturations are obtained at all the pixels.

After the hemoglobin concentrations and the oxygen saturations are obtained at all the pixels (Step ST130), the reference value calculation section 84 calculates the average values of the hemoglobin concentrations and the oxygen saturations of every frame (Step ST140). The calculated average value of a hemoglobin concentration is set as the reference value of a hemoglobin concentration, and the calculated average value of an oxygen saturation is set as the reference value of an oxygen saturation likewise (Step ST150). After the reference value is updated, the mode is automatically switched to the ischemia evaluation mode from the reference value calculation mode. The monitor displays that the reference value is updated, so that the operator knows that the reference value is updated and the mode is switched to the ischemia evaluation mode.

In a case where the operator does not press the scope button of the reference value-calculation-instruction part 28b (NO in Step ST110), the reference value used in the previous time is set as the reference value (Step ST160). The monitor displays that the reference value of the previous time is set, so that the operator knows that the reference value of the previous time is set.

After that, the operator observes the position, which is marked by the clips, by the endoscope device 22 for lumen in the ischemia evaluation mode of the endoscope device 32 for abdominal cavity. The actual measurement values of the hemoglobin concentration and the oxygen saturation of an object to be observed, which is observed from the abdominal cavity side, are calculated. Since a method of calculating these actual measurement values is the same as the above-mentioned method, the method will be omitted (Step ST170 and Step ST180). The relative value calculation section 75 calculates the relative value ΔcHb of a hemoglobin concentration by a difference between the reference value of a hemoglobin concentration, which is obtained in advance, and the actual measurement value of the hemoglobin concentration of the object to be observed. Likewise, the relative value calculation section 75 calculates the relative value $\Delta StO_2$ of an oxygen saturation by a difference between the reference value of an oxygen saturation, which is obtained in advance, and the actual measurement value of the oxygen saturation of the object to be observed (Step ST190).

The image generation section 76 obtains color difference signals Cb and Cr, which corresponds to the relative value ΔcHb of a hemoglobin concentration, with reference to the color table 96 by the calculated relative value ΔcHb of a hemoglobin concentration and the calculated relative value $\Delta StO_2$ of an oxygen saturation. Then, the image generation section 76 generates a hemoglobin concentration image, in which the relative value ΔcHb of a hemoglobin concentration is represented with a pseudo color, from the obtained color difference signals Cb and Cr and luminance Y to which the G1m image signal and the G2m image signal obtained from the first light emission are assigned (Step ST200, see FIG. 18). Further, likewise, the image generation section 76 generates an oxygen saturation image, in which the relative value $\Delta StO_2$ of an oxygen saturation is represented with a pseudo color, using the color table 97 (see FIG. 19). Furthermore, likewise, the image generation section 76 generates a determination index image, in which the relative value ΔcHb of a hemoglobin concentration and the relative value $\Delta StO_2$ of an oxygen saturation are represented with pseudo colors, using the luminance table 98 and the color table 99 (see FIGS. 21 and 22). The generated hemoglobin concentration image, the generated oxygen saturation image, or the generated determination index image is displayed on the display device 12 (Step ST200).

Since at least one image of the hemoglobin concentration image, the oxygen saturation image, or the determination index image is displayed on the display device 12, the operator specifies the position of the tumor portion and confirms an oxygen saturation, the state of ischemia, and the like near the tumor portion. For example, the operator can confirm that a portion where an oxygen saturation is lowered by the clips is the tumor portion. Further, information about both the state of oxygen and the state of ischemia near the tumor portion is obtained by the endoscope device 32 for abdominal cavity. Accordingly, even though there is a portion where an oxygen saturation is low, the operator can select a boundary between an ischemic region and a normal region, avoid an ischemic region, avoid a position where congestion and ischemia are mixed, or select a position where congestion and ischemia are uniform, that is, can determine a resection position or an anastomosis position where the failure of the sutures more hardly occurs. In a case where, newly, the operator desires to reset the reference values and to display an image from which an ischemic region or the like is more easily determined, the operator calculates reference values again and repeats a series of operations (NO in Step ST210). After the completion of treatment, the operator extracts the endoscope device 32 for abdominal cavity from the patient 40 and performs a procedure for completing the surgery (YES in Step ST210).

The determination index image is generated and displayed on the basis of the relative value $\Delta StO_2$ of an oxygen saturation and the relative value ΔcHb of a hemoglobin concentration in the embodiment, but the endoscope system 10 may be provided with an index value calculation unit (not shown) that calculates a congestion index value representing the degree of congestion or an ischemic index value representing the degree of ischemia. In a case where the congestion index value or the ischemic index value is displayed on the display device 12 together with the oxygen saturation image, it is easy to determine whether a region where an oxygen saturation is low is a congestive region or an ischemic region.

In regard to the congestion index value and the ischemic index value, it is preferable that, for example, the congestion index value and the ischemic index value are set to be larger as the relative value $\Delta StO_2$ of an oxygen saturation is negative and the absolute value of the relative value $\Delta StO_2$ of an oxygen saturation is larger. As the relative value ΔcHb of a hemoglobin concentration is positive and the absolute value of the relative value ΔcHb of a hemoglobin concentration is larger, the congestion index value is set to be larger. On the other hand, as the relative value ΔcHb of a hemoglobin concentration is negative and the absolute value of the relative value ΔcHb of a hemoglobin concentration is larger, the ischemic index value is set to be larger.

In the embodiments, the hardware structures of processing units, which perform various kinds of processing, such as the central control unit 56, the image acquisition unit 57, the image processing unit 58, and the display control unit 59, are various processors to be described below. Various processors include: a central processing unit (CPU) that is a general-purpose processor functioning as various processing units by executing software (program); a programmable logic device (PLD) that is a processor of which the circuit configuration can be changed after manufacture, such as a field programmable gate array (FPGA); a dedicated electrical circuit (graphical processing unit: GPU) that is a processor having circuit configuration designed exclusively to perform various kinds of processing; and the like.

One processing unit may be formed of one of these various processors, or may be formed of a combination of two or more same kind or different kinds of processors (for example, a combination of a plurality of FPGAs, a combination of a CPU and an FPGA, and a combination of a GPU and a CPU). Further, a plurality of processing units may be formed of one processor. As an example where a plurality of processing units are formed of one processor, first, there is an aspect where one processor is formed of a combination of one or more CPUs and software as typified by a computer, such as a client or a server, and functions as a plurality of processing units. Second, there is an aspect where a processor implementing the functions of the entire system, which includes a plurality of processing units, by one integrated circuit (IC) chip as typified by System On Chip (SoC) or the like is used. In this way, various processing units are formed using one or more of the above-mentioned various processors as hardware structures.

In addition, the hardware structures of these various processors are more specifically electrical circuitry where circuit elements, such as semiconductor elements, are combined.

EXPLANATION OF REFERENCES

10: endoscope system
12: display device
14: input device
20: endoscope system for lumen
21: light source device for lumen
22: endoscope device for lumen
23: processor device for lumen
24a: endoscope operation unit for lumen
24b: endoscope-insertion part for lumen
25: scope-distal end part
26: forceps channel
26a: forceps inlet
26b: forceps outlet
27: bendable part
28a: mode switching part
28b: reference value-calculation-instruction part
29: angle knob
30: endoscope system for abdominal cavity
31: light source device for abdominal cavity
32: endoscope device for abdominal cavity
33: processor device for abdominal cavity
34: endoscope-insertion part for abdominal cavity
35: endoscope-distal end part for abdominal cavity
36: foot switch
37: insufflation device
38: treatment tool
39a, 39b: trocar
40: patient
40a: inside of abdominal cavity
41: light source
41a: BS-LED
41d: BL-LED
41c: G-LED
41d: R-LED
42: light source control unit
43: light guide
44a: illumination optical system
44b: image pickup optical system
45: illumination lens
46: objective lens
48: image pickup sensor
49: image pickup surface
51: pixel
52: B-color filter
53: G-color filter
54: R-color filter
55: image pickup control unit
56: central control unit
57: image acquisition unit
58: image processing unit
59: display control unit
59a: display image selection section
61: DSP
62: noise reduction section
63: conversion section
71: normal image processing section
72: functional image processing section
73: measurement value calculation section
74: reference value-calculation-instruction receiving section
75: relative value calculation section
76: image generation section
81: signal ratio calculation section
82: correlation storage section
83: actual measurement value calculation section
84: reference value calculation section
85, 86, 91: graph
91a: light absorption coefficient of oxyhemoglobin
91b: light absorption coefficient of reduced hemoglobin
93: lower limit line
94: upper limit line
95a: Cr
95b: Cb
95c: luminance value
96: color table
97: color table
98: luminance table
99: color table
101: hemoglobin concentration image
102: oxygen saturation image
103: determination index image
X direction: row direction
Y direction: column direction
ST100 to ST210: Step

What is claimed is:
1. An endoscope system comprising:
a processor configured to function as:
a measurement value calculation section that calculates a first actual measurement value of a concentration of hemoglobin included in a first object to be observed and a first actual measurement value of an oxygen saturation of hemoglobin included in the first object to be observed on the basis of a plurality of first spectral images obtained by imaging the first object to be observed, of which the state of ischemia is desired to be evaluated;

a reference value calculation section that calculates a second actual measurement value of a concentration of hemoglobin included in a second object to be observed, which is different from the first object to be observed, and a second actual measurement value of an oxygen saturation of hemoglobin included in the second object to be observed on the basis of a plurality of second spectral images obtained by imaging the second object to be observed, of which the state of ischemia is desired to be set as a reference, to obtain a reference value of the concentration of hemoglobin included in the second object to be observed and a reference value of the oxygen saturation of hemoglobin included in the second object to be observed;

a relative value calculation section that calculates a relative value of the concentration and a relative value of the oxygen saturation on the basis of the first actual measurement value of the concentration, the reference value of the concentration of hemoglobin included in the second object to be observed, the first actual measurement value of the oxygen saturation, and the reference value of the oxygen saturation of hemoglobin included in the second object to be observed; and an image generation section that generates a relative value image obtained from imaging of at least one of the relative value of the concentration or the relative value of the oxygen saturation; and a display that displays the relative value image.

2. The endoscope system according to claim 1, wherein the reference value calculation section calculates the reference value of the concentration and the reference value of the oxygen saturation on the basis of the plurality of second spectral images.

3. The endoscope system according to claim 2, wherein the processor is further configured to function as a reference value-calculation-instruction receiving section that receives an instruction to calculate the reference value of the concentration and the reference value of the oxygen saturation, and wherein the reference value calculation section calculates the reference value of the concentration and the reference value of the oxygen saturation on the basis of the instruction.

4. The endoscope system according to claim 2, wherein the reference value calculation section calculates the reference value of the concentration or the reference value of the oxygen saturation by averaging second actual measurement values of the concentration calculated for pixels of the plurality of second spectral images or second actual measurement values of the oxygen saturation calculated for pixels of the plurality of second spectral images.

5. The endoscope system according to claim 1, wherein the processor is further configured to function as a signal ratio calculation section that obtains a signal ratio dependent on the concentration on the basis of the plurality of first spectral images or the plurality of second spectral images, a correlation storage section that stores a correlation between the concentration and the signal ratio, and an actual measurement value calculation section that calculates the first actual measurement value or the second actual measurement value of the concentration corresponding to the signal ratio on the basis of the correlation.

6. The endoscope system according to claim 2, wherein the first spectral images are images that are obtained from image pickup of a first object to be observed including a lesion, and the second spectral images are images that are obtained from image pickup of a second object to be observed not including a lesion.

7. The endoscope system according to claim 1, wherein the relative value image includes a hemoglobin concentration image that is obtained from imaging of the relative value of the concentration, an oxygen saturation image that is obtained from imaging of the relative value of the oxygen saturation, and a determination index image that is obtained from imaging of the relative value of the concentration and the relative value of the oxygen saturation.

8. The endoscope system according to claim 7, wherein the image generation section generates the hemoglobin concentration image by converting the relative value of the concentration into a pseudo-color image using a color table for the concentration that stores pseudo-color information changing according to the concentration, and generates the oxygen saturation image by converting the relative value of the oxygen saturation into a pseudo-color image using a color table for the oxygen saturation that stores pseudo-color information changing according to the oxygen saturation.

9. The endoscope system according to claim 7, wherein the image generation section generates the determination index image by assigning the relative value of the concentration to a luminance channel and assigning the relative value of the oxygen saturation to two color difference channels.

10. The endoscope system according to claim 7, wherein the processor is further configured to function as a display image selection section that receives a selection of a display image, and wherein the display displays at least one of the hemoglobin concentration image, the oxygen saturation image, or the determination index image according to the selection received by the display image selection section.

11. The endoscope system according to claim 10, wherein the display displays both the hemoglobin concentration image and the oxygen saturation image on the same screen.

12. A processor device comprising:
a processor configured to function as:
an image acquisition unit that receives a plurality of first spectral images from an endoscope device acquiring the plurality of first spectral images;

a measurement value calculation section that calculates a first actual measurement value of a concentration of hemoglobin included in a first object to be observed and a first actual measurement value of an oxygen saturation of hemoglobin included in the first object to be observed on the basis of the plurality of first spectral images obtained by imaging the first object to be observed, of which the state of ischemia is desired to be evaluated;

a reference value calculation section that calculates a second actual measurement value of a concentration of hemoglobin included in a second object to be observed, which is different from the first object to be observed, and a second actual measurement value of an oxygen saturation of hemoglobin included in the second object to be observed on the basis of a plurality of second spectral images obtained by imaging the second object to be observed, of which the state of ischemia is desired to be set as a reference, to obtain a reference value of the concentration of hemoglobin included in the second object to be observed and a reference value of the oxygen saturation of hemoglobin included in the second object to be observed;

a relative value calculation section that calculates a relative value of the concentration and a relative value of the oxygen saturation on the basis of the first actual measurement value of the concentration, the reference value of the concentration of hemoglobin included in the second object to be observed, the first actual measurement value of the oxygen saturation, and the reference value of the oxygen saturation of hemoglobin included in the second object to be observed; and an image generation section that generates a relative value image obtained from imaging of at least one of the relative value of the concentration and/or the relative value of the oxygen saturation.

13. A method of operating an endoscope system comprising:

an actual measurement value calculation step of causing a processor to calculate a first actual measurement value of a concentration of hemoglobin included in a first object to be observed and a first actual measurement value of an oxygen saturation of hemoglobin included in the first object to be observed on the basis of a plurality of first spectral images obtained by imaging the first object to be observed, of which the state of ischemia is desired to be evaluated;

a reference value calculation step of causing the processor to calculate a second actual measurement value of a concentration of hemoglobin included in a second object to be observed, which is different from the first object to be observed, and a second actual measurement value of an oxygen saturation of hemoglobin included in the second object to be observed on the basis of a plurality of second spectral images obtained by imaging the second object to be observed, of which the state of ischemia is desired to be set as a reference, to obtain a reference value of the concentration of hemoglobin included in the second object to be observed and a reference value of the oxygen saturation of hemoglobin included in the second object to be observed;

a relative value calculation step of causing the processor to calculate a relative value of the concentration and a relative value of the oxygen saturation on the basis of the first actual measurement value of the concentration, the reference value of the concentration of hemoglobin included in the second object to be observed, the first actual measurement value of the oxygen saturation, and the reference value of the oxygen saturation of hemoglobin included in the second object to be observed;

an image generation step of causing the processor to generate a relative value image obtained from the imaging of the relative value of the concentration and/or the relative value of the oxygen saturation; and a display step of causing a display to display the relative value image.

* * * * *